(12) United States Patent
Tardif

(10) Patent No.: US 8,163,699 B2
(45) Date of Patent: Apr. 24, 2012

(54) METHOD FOR THE TREATMENT OF VALVULAR DISEASE

(75) Inventor: Jean-Claude Tardif, Laval (CA)

(73) Assignee: Montreal Heart Institute, Montreal, QC (CA)

( * ) Notice: Subject to any disclaimer, the term of this patent is extended or adjusted under 35 U.S.C. 154(b) by 0 days.

(21) Appl. No.: 12/227,872

(22) PCT Filed: May 23, 2007

(86) PCT No.: PCT/CA2007/000895
§ 371 (c)(1),
(2), (4) Date: Dec. 1, 2008

(87) PCT Pub. No.: WO2007/137400
PCT Pub. Date: Dec. 6, 2007

(65) Prior Publication Data
US 2009/0186808 A1    Jul. 23, 2009

Related U.S. Application Data

(60) Provisional application No. 60/809,850, filed on Jun. 1, 2006.

(51) Int. Cl.
*A61P 9/10* (2006.01)
*A61P 3/06* (2006.01)
*A61K 38/16* (2006.01)
*C07K 14/775* (2006.01)

(52) U.S. Cl. ........ 514/16.4; 514/1.9; 514/7.4; 514/21.4; 530/326; 530/359

(58) Field of Classification Search ........................ None
See application file for complete search history.

(56) References Cited

U.S. PATENT DOCUMENTS

| | | |
|---|---|---|
| 4,229,360 A | 10/1980 | Schneider et al. |
| 4,411,894 A | 10/1983 | Schrank et al. |
| 4,643,988 A | 2/1987 | Segrest et al. |
| 4,857,319 A | 8/1989 | Crowe et al. |
| 4,880,635 A | 11/1989 | Janoff et al. |
| 5,733,879 A | 3/1998 | Rosseneu et al. |
| 5,972,890 A | 10/1999 | Lees et al. |
| 6,004,925 A | 12/1999 | Dasseux et al. |
| 6,037,323 A | 3/2000 | Dasseux et al. |
| 6,046,166 A | 4/2000 | Dasseux et al. |

(Continued)

FOREIGN PATENT DOCUMENTS

EP    0162414    11/1985

(Continued)

OTHER PUBLICATIONS

Bender, Heart Valve Disease, Chapter 13 in the Yale University School of Medicine Heart Book, 1992, pp. 167-175).*

(Continued)

*Primary Examiner* — Bridget E Bunner
*Assistant Examiner* — Zachary Howard
(74) *Attorney, Agent, or Firm* — Cooley LLP

(57) ABSTRACT

A method for treating valvular stenosis. The method involves the administration of a therapeutically effective amount of a reverse lipid (in particular cholesterol) transport agonist to a mammal. Most preferred is an Apolipoprotein A-1 mimetic peptide/phospholipid complex, the peptide of which is defined by the amino acid sequence of SEQ ID NO 1.

16 Claims, 3 Drawing Sheets

U.S. PATENT DOCUMENTS

| | | |
|---|---|---|
| 6,265,377 B1 | 7/2001 | Dasseux et al. |
| 6,287,590 B1 | 9/2001 | Dasseux |
| 6,329,341 B1 | 12/2001 | Dasseux et al. |
| 6,376,464 B1 | 4/2002 | Dasseux et al. |
| 6,455,088 B1 | 9/2002 | Dasseux |
| 6,506,799 B1 | 1/2003 | Dasseux |
| 6,518,412 B1 | 2/2003 | Dasseux et al. |
| 6,573,239 B1 | 6/2003 | Dasseux et al. |
| 6,602,854 B1 | 8/2003 | Dasseux et al. |
| 6,630,450 B1 | 10/2003 | Dasseux et al. |
| 6,716,816 B1 | 4/2004 | Dasseux et al. |
| 6,734,169 B2 | 5/2004 | Dasseux et al. |
| 6,743,778 B2 | 6/2004 | Kohno |
| 6,753,313 B1 | 6/2004 | Dasseux et al. |
| 6,844,327 B2 | 1/2005 | Dasseux et al. |
| 6,900,177 B1 | 5/2005 | Dasseux et al. |
| 7,157,425 B2 | 1/2007 | Dasseux et al. |
| 7,189,411 B2 | 3/2007 | Dasseux |
| 7,189,689 B2 | 3/2007 | Dasseux et al. |
| 7,211,565 B2 | 5/2007 | Dasseux et al. |
| 7,250,407 B2 | 7/2007 | Dasseux et al. |
| 7,273,848 B2 | 9/2007 | Dasseux et al. |
| 7,307,058 B2 | 12/2007 | Dasseux et al. |
| 7,312,190 B2 | 12/2007 | Dasseux et al. |
| 2003/0045460 A1 | 3/2003 | Fogelman et al. |
| 2003/0109442 A1 | 6/2003 | Bisgaier |
| 2003/0171277 A1 | 9/2003 | Fogelman et al. |
| 2004/0067873 A1 | 4/2004 | Dasseux et al. |
| 2006/0069030 A1 | 3/2006 | Bachovchin |
| 2006/0217312 A1 | 9/2006 | Dasseux et al. |
| 2006/0252694 A1 | 11/2006 | Dasseux et al. |
| 2007/0167351 A1 | 7/2007 | Dasseux et al. |
| 2007/0197442 A1 | 8/2007 | Pressler et al. |
| 2008/0050351 A1 | 2/2008 | Dasseux et al. |
| 2008/0058270 A1 | 3/2008 | Dasseux et al. |
| 2008/0138284 A1 | 6/2008 | Brewer et al. |
| 2008/0214434 A1 | 9/2008 | Stroes |
| 2008/0269111 A1 | 10/2008 | Dasseux et al. |
| 2009/0081293 A1 | 3/2009 | Murase et al. |
| 2010/0267461 A1 | 10/2010 | Dasseux et al. |
| 2011/0092430 A1 | 4/2011 | Tardif |

FOREIGN PATENT DOCUMENTS

| | | |
|---|---|---|
| JP | 61152632 | 7/1986 |
| WO | WO 93/25581 | 12/1993 |
| WO | WO 94/13819 | 6/1994 |
| WO | WO 96/04916 | 2/1996 |
| WO | WO 96/37608 | 11/1996 |
| WO | WO 99/16409 | 4/1999 |
| WO | WO 99/16459 | 4/1999 |
| WO | WO 03/026492 | 4/2003 |
| WO | WO 2007/004060 | 1/2007 |
| WO | WO 2007/137400 | 12/2007 |
| WO | WO 2008/094905 | 8/2008 |
| WO | WO 2008/156873 | 12/2008 |

OTHER PUBLICATIONS

Yilmaz et al, 2004. Am Heart J. 147: 915-918.*
Kaul et al., "Intramural delivery of recombinant apolipoprotein A-I$_{Milano}$/phospholipid complex (ETC-216) inhibits in-stent stenosis in porcine coronary arteries," Circulation 107:2551-2554, 2003.
Ameli et al., "Recombinant apolipoprotein A-I Milano reduces intimal thickening after balloon injury in hypercholesterolemic rabbits," Circulation. Oct;90(4):1935-41, 1994.
Anantharamaiah et al., "Use of synthetic peptide analogues to localize lecithin:cholesterol acyltransferase activating domain in apolipoprotein A-I," Arteriosclerosis Jan.-Feb.;10(1):95-105, 1990.
Bodary et al., "Gene transfer of an ApoA-I mimetic peptide reduces atherosclerosis in mice," J Am Coll Cardiol 43(SupplA):465A-6, 2004.
Busseuil et al., "Late neointimal tissue growth behind the stent after intravascular gamma-radiation," Int J Radiat Oncol Biol Phys. Jan. 1;58(1):259-66, 2004.
Carabello, "Clinical practice—Aortic stenosis," N Engl J Med. Feb. 28;346(9):677-82, 2002.
Cowell et al., "A randomized trial of intensive lipid-lowering therapy in calcific aortic stenosis," N Engl J Med. Jun. 9;352(23):2389-97, 2005.
Drolet et al., "Experimental aortic valve stenosis in rabbits," J Am Coll Cardiol. Apr. 2;41(7):1211-7, 2003.
Freeman et al., "Spectrum of calcific aortic valve disease: pathogenesis, disease progression, and treatment strategies," Circulation. Jun. 21;111(24):3316-26, 2005.
Khan et al., "Single dose intravenous infusion of ETC-642, a 22-mer ApoA-I analogue and phospholipids complex, elevates HDL-C in atherosclerosis patients," Circulation 108(Suppl):IV:563-4, 2003.
Meyers et al., "Pharmacologic augmentation of high-density lipoproteins: mechanisms of currently available and emerging therapies," Curr Opin Cardiol. Jul;20(4):307-12, 2005.
Navab et al., "Apolipoprotein A-I mimetic peptides,"_Arterioscler Thromb Vasc Biol. Jul. 2005;25(7):1325-31. Epub Apr. 14. Review, 2005.
Navab et al., "Human apolipoprotein A-I and A-I mimetic peptides: potential for atherosclerosis reversal," Curr Opin Lipidol. Dec. ;15(6):645-9, 2004.
Nissen et al., "Effect of recombinant ApoA-I Milano on coronary atherosclerosis in patients with acute coronary syndromes: a randomized controlled trial," JAMA. Nov. 5;290(17):2292-300, 2003.
Nissen et al., "Effect of very high-intensity statin therapy on regression of coronary atherosclerosis: the Asteroid trial," JAMA. Apr. 5;295(13):1556-65. Epub 2006 Mar. 13, 2006.
Rossebo et al., "Hyperlipidaemia and aortic valve disease," Curr Opin Lipidol. Aug.;15(4):447-51, 2004.
Shah et al., "High-dose recombinant apolipoprotein A-I(milano) mobilizes tissue cholesterol and rapidly reduces plaque lipid and macrophage content in apolipoprotein e-deficient mice. Potential implications for acute plaque stabilization," Circulation. Jun. 26;103(25):3047-50, 2001.
Srinivas et al., "Inhibition of virus-induced cell fusion by apolipoprotein A-I and its amphipathic peptide analogs," J Cell Biochem. Feb.;45(2):224-37, 1991.
Tardif et al., "Effects of reconstituted high-density lipoprotein infusions on coronary atherosclerosis: a randomized controlled trial," JAMA. Apr. 18;297(15):1675-82. Epub 2007 Mar. 26, 2007.
Venkatachalapathi et al., Molecular Conformation and Biological Interactions (Indian Academy of Sciences, Bangalore) pp. 585-596, 1991.
Copeland, "Substitution of proline with pipecolic acid at the scissile bond converts a peptide substrate of HIV proteinase into a selective inhibitor," Biochem Biophys Res Commun 169(1):310-4, 1990.
Busseuil et al., "Regression of aortic valve stenosis by ApoA-I mimetic peptide infusions in rabbits," Br J Pharmacol 154(4):765-73, 2008.
Chan et al., "Effect of Lipid lowering with rosuvastatin on progression of aortic stenosis: results of the aortic stenosis progression observation: measuring effects of rosuvastatin (Astronomer) trial," Circulation 121(2):306-14, 2010.
Newby et al., "Emerging medical treatments for aortic stenosis: statins, angiotensin converting enzyme inhibitors, or both," Heart 92(6):729-34, 2006.
Rajamannan, "Calcific aortic stenosis: lessons learned from experimental and clinical studies," Arterioscler Thromb Vasc Biol 29(2):162-8, 2009.
Rossebo et al., "Intensive lipid lowering with simvastatin and ezetimibe in aortic stenosis," N Engl J Med 359(13):1343-56, 2008.
Tardif, "Method and Compound for the Treatment of Valvular Disease," U.S. Appl. No. 12/956,615, filed Nov. 30, 2010.
International Search Report and Written Opinion of the International Searching Authority mailed on Jul. 16, 2010 in connection with PCT/US10/24096.
Brown, et al. HDL as a treatment target. *J Clin Lipidol* 4, 5-16 (2010).
Lee, et al. *Expert Rev Cardiovasc Ther* 8, 1325-1334 (2010).
Brewer, et al. HDL metabolism and the role of HDL in the treatment of high-risk patients with cardiovascular disease. *Curr Cardiol Rep* 9, 486-492 (2007).
Schwartz, et al. Preferential utilization of free cholesterol from high-density lipoproteins for biliary cholesterol secretion in man. *Science* 200, 62-64 (1978).

Martinez, et al. Ectopic beta-chain of ATP synthase is an apolipoprotein A-I receptor in hepatic HDL endocytosis. *Nature* 421, 75-79 (2003).

Jacquet, et al. The nucleotide receptor P2Y13 is a key regulator of hepatic high-density lipoprotein (HDL) endocytosis. *Cell Mol Life Sci* 62, 2508-2515 (2005).

Fabre, et al. P2Y13 receptor is critical for reverse cholesterol transport. *Hepatology* 52, 1477-1483 (2010).

Kim, et al. Synthesis of pyridoxal phosphate derivatives with antagonist activity at the P2Y13 receptor. *Biochem Pharmacol* 70, 266-274 (2005).

Godin, et al. Remodeling of carotid artery is associated with increased expression of matrix metalloproteinases in mouse blood flow cessation model. *Circulation* 102, 2861-2866 (2000).

Ivan, et al. Expansive arterial remodeling is associated with increased neointimal macrophage foam cell content: the murine model of macrophage-rich carotid artery lesions. *Circulation* 105, 2686-2691 (2002).

Lessner, et al. Compensatory vascular remodeling during atherosclerotic lesion growth depends on matrix metalloproteinase-9 activity. *Arterioscler Thromb Vasc Biol* 24, 2123-2129 (2004).

Khera, et al. Cholesterol efflux capacity, high-density lipoprotein function, and atherosclerosis. *N Engl J Med* 364, 127-135 (2011).

Degoma, et al. Beyond high-density lipoprotein cholesterol levels evaluating high-density lipoprotein function as influenced by novel therapeutic approaches. *J Am Coll Cardiol* 51, 2199-2211 (2008).

Braschi et al. Apolipoprotein A-I charge and conformation regulate the clearance of reconstituted high density lipoprotein in vivo. J Lipid Res. 1999. 40(3):522-32.

Epand et al. Studies of synthetic peptide analogs of the amphipathic helix. Effect of charge distribution, hydrophobicity, and secondary structure on lipid association and lecithin:cholesterol acyltransferase activation. J Biol Chem. 1987. 262(19):9389-96.

Guasch et al. Charge selectivity of the glomerular filtration barrier in healthy and nephrotic humans. J Clin Invest. 1993. 92(5):2274-82.

Anantharamaiah, "Synthetic peptide analogs of apolipoproteins," Methods Enzymol 128:627-47 (1986).

Anantharamaiah et al., "Studies of synthetic peptide analogs of the amphipathic helix. Structure of complexes with dimyristoyl phosphatidylcholine," J Biol Chem 260(18):10248-55 (1985).

Anantharamaiah et al., "Role of amphipathic helixes in HDL structure/function," Adv Exp Med Biol 285:131-40 (1991).

Badimon et al., "Regression of atherosclerotic lesions by high density lipoprotein plasma fraction in the cholesterol-fed rabbit," J Clin Invest 85(4):1234-41 (1990).

Barrans et al., "Pre-beta HDL: structure and metabolism," Biochim Biophys Acta 1300(2):73-85 (1996).

Beitz et al., "Does a HDL injection reduce the development of serum hyperlipidemia and progression of fatty streaks in cholesterol fed rabbits?" Prostaglandins Leukot Essent Fatty Acids 147(2):149-52 (1992).

Berard et al., "High plasma HDL concentrations associated with enhanced atherosclerosis in transgenic mice overexpressing lecithin-cholesteryl acyltransferase," Nat Med 3(7):744-9 (1997).

Blondelle et al., "Influence of tryptophan residues on melittin's hemolytic activity," Biochim Biophys Acta 1202(2):331-6 (1993).

Brasseur et al., "Differentiation of lipid-associating helices by use of three-dimensional molecular hydrophobicity potential calculations," J Biol Chem 266(24):16120-7 (1991).

Brasseur et al., "Mode of assembly of amphipathic helical segments in model high-density lipoproteins," Biochim Biophys Acta 1043(3):245-52 (1990).

Brasseur et al., "Synthetic model peptides for apolipoproteins. I. Design and properties of synthetic model peptides for the amphipathic helices of the plasma apolipoproteins," Biochim Biophys Acta 1170(1):1-7 (1993).

Brouillette et al., "Structural models of human apolipoprotein A-I," Biochim Biophys Acta 1256(2):103-29 (1995).

Burkey et al., "Overexpression of human apolipoprotein A-I in transgenic rats and the hyperlipoproteinemia associated with experimental nephrosis," J Lipid Res 36(7):1463-73 (1995).

Cheung et al., "Altered particle size distribution of apolipoprotein A-I-containing lipoproteins in subjects with coronary artery disease," J Lipid Res 32(3):383-94 (1991).

Collet et al., "Evolution of mammalian apolipoprotein A-I and conservation of antigenicity: correlation with primary and secondary structure," J Lipid Res Apr. 1997;38(4):634-44 (1997).

Corijn et al., "Synthetic model peptides for apolipoproteins. II. Characterization of the discoidal complexes generated between phospholipids and synthetic model peptides for apolipoproteins," Biochim Biophys Acta 1170(1):8-16 (1993).

Davidson et al., "The influence of apolipoprotein structure on the efflux of cellular free cholesterol to high density lipoprotein," J Biol Chem 269(37):22975-82 (1994).

Davidson et al., "The role of apolipoprotein AI domains in lipid binding," Proc Natl Acad Sci U S A 93(24):13605-10 (1996).

Demoor et al., "Branched synthetic constructs that mimic the physico-chemical properties of apolipoprotein AI in reconstituted high-density lipoproteins," Eur J Biochem 239(1):74-84 (1996).

Dufourcq et al., "Morphological changes of phosphatidylcholine bilayers induced by melittin: vesicularization, fusion, discoidal particles," Biochim Biophys Acta 859(1):33-48 (1986).

Duverger et al., "Inhibition of atherosclerosis development in cholesterol-fed human apolipoprotein A-I-transgenic rabbits," Circulation 94(4):713-7 (1996).

Duverger et al., "Transgenic rabbits expressing human apolipoprotein A-I in the liver," Arterioscler Thromb Vasc Biol 16(12):1424-9, 1996.

Emmanuel et al., "Identification of specific amphipathic alpha-helical sequence of human apolipoprotein A-IV involved in lecithin:cholesterol acyltransferase activation," J Biol Chem 269(47):29883-90 (1994).

Epand et al., "Mechanisms for the modulation of membrane bilayer properties by amphipathic helical peptides," Biopolymers 37(5):319-38 (1995).

Esposito et al., "Lysine as helix C-capping residue in a synthetic peptide," Biopolymers 41(1):27-35 (1997).

Fielding et al., "Molecular physiology of reverse cholesterol transport," J Lipid Res 36(2):211-28 (1995).

Fournier et al., "Role of HDL phospholipid in efflux of cell cholesterol to whole serum: studies with human apoA-I transgenic rats," J Lipid Res 37(8):1704-11 (1996).

Francone et al., "Expression of human lecithin-cholesterol acyltransferase in transgenic mice. Effect of human apolipoprotein AI and human apolipoprotein all on plasma lipoprotein cholesterol metabolism," J Clin Invest 96(3):1440-8 (1995).

Fruchart et al., "Apolipoprotein A-containing lipoprotein particles: physiological role, quantification, and clinical significance," Clin Chem 38(6):793-7 (1992).

Fukushima et al., "Chain length-function correlation of amphiphilic peptides. Synthesis and surface properties of a tetratetracontapeptide segment of apolipoprotein A-I," J Biol Chem 255(22):10651-7 (1980).

Garber et al., "Turnover of synthetic class A amphipathic peptide analogues of exchangeable apolipoproteins in rats. Correlation with physical properties," Arterioscler Thromb 12(8):886-94 (1992).

Gordon et al., "High-density lipoprotein cholesterol and cardiovascular disease. Four prospective American studies," Circulation 79(1):8-15 (1989).

Gordon et al., "High-density lipoprotein—the clinical implications of recent studies," N Engl J Med 321(19):1311-6 (1989).

Groebke et al., "Template-nucleated alanine-lysine helices are stabilized by position-dependent interactions between the lysine side chain and the helix barrel," Proc Natl Acad Sci U S A 93(9):4025-9 (1996).

Holvoet et al., "Phospholipid binding and lecithin-cholesterol acyltransferase activation properties of apolipoprotein A-I mutants," Biochemistry 34(41):13334-42 (1995).

Huygheus-Despointes et al., "Measuring the strength of side-chain hydrogen bonds in peptide helices: the Gln.Asp (i, i+4) interaction," Biochemistry 34(41):13267-71 (1995).

Ji et al., "Properties of an N-terminal proteolytic fragment of apolipoprotein AI in solution and in reconstituted high density lipoproteins," J Biol Chem 270(19):11290-7 (1995).

Johnson et al., "Single bilayer liposomes," Biochim Biophys Acta 233(3):820-6 (1971).

Jonas, "Reconstitution of high-density lipoproteins," Methods Enzymol 128:553-82 (1986).

Kaiser et al., "Color test for detection of free terminal amino groups in the solid-phase synthesis of peptides," Anal Biochem 34(2):595-8 (1970).

Kaiser et al., "Secondary structures of proteins and peptides in amphiphilic environments. (A review)," Proc Natl Acad Sci U S A 80(4):1137-43 (1983).

Kannelis et al., "Studies of synthetic peptide analogs of the amphipathic helix. Effect of charged amino acid residue topography on lipid affinity," J Biol Chem 255(23):11464-72 (1980).

Koizumi et al., "Behavior of human apolipoprotein A-I: phospholipid and apoHDL:phospholipid complexes in vitro and after injection into rabbits," J Lipid Res 29(11):1405-15 (1988).

Kneib-Cordonnier et al., Int. J. Peptide Protein Res. 35:527-538 (1990).

Knott et al., "Human apolipoprotein B: structure of carboxyl-terminal domains, sites of gene expression, and chromosomal localization," Science 230(4721):37-43 (1985).

Labeur et al., "Design of a new class of amphipathic helical peptides for the plasma apolipoproteins that promote cellular cholesterol efflux but do not activate LCAT," Arterioscler Thromb Vasc Biol 17(3):580-8 (1997).

Lacko et al., "International Symposium on the Role of HDL in Disease Prevention: report on a meeting," J Lipid Res 38(6):1267-73 (1997).

Li et al., "Alpha-helical, but not beta-sheet, propensity of proline is determined by peptide environment," Proc Natl Acad Sci U S A 93(13):6676-81 (1996).

Lins et al., "Enzymatic hydrolysis of reconstituted dimyristoylphosphatidylcholine-apo A-I complexes," Biochim Biophys Acta 1151(2):137-42 (1993).

Liu et al., "Human apolipoprotein A-I prevents atherosclerosis associated with apolipoprotein[a] in transgenic mice," J Lipid Res 35(12):2263-7 (1994).

Lund-Katz et al., "Nuclear magnetic resonance investigation of the interactions with phospholipid of an amphipathic alpha-helix-forming peptide of the apolipoprotein class," J Biol Chem 265(21):12217-23 (1990).

Lund-Katz et al., "Microenvironments of basic amino acids in amphipathic alpha-helices bound to phospholipid: 13C NMR studies using selectively labeled peptides," Biochemistry 34(28):9219-26 (1995).

Marqusee et al., "Helix stabilization by Glu- . . . Lys+ salt bridges in short peptides of de novo design," Proc Natl Acad Sci U S A 84(24):8898-902 (1987).

Mendez et al., "Synthetic amphipathic helical peptides that mimic apolipoprotein A-I in clearing cellular cholesterol," J Clin Invest 94(4):1698-705 (1994).

Mezdour et al., "Exogenous supply of artificial lipoproteins does not decrease susceptibility to atherosclerosis in cholesterol-fed rabbits," Atherosclerosis 113(2):237-46(1995).

Miller et al., "Associations of high-density lipoprotein subclasses and apolipoproteins with ischemic heart disease and coronary atherosclerosis," Am Heart J 113(2 Pt 2):589-97 (1987).

Minnich et al., "Site-directed mutagenesis and structure-function analysis of the human apolipoprotein A-I. Relation between lecithin-cholesterol acyltransferase activation and lipid binding," J Biol Chem 267(23):16553-60 (1992).

Mishra et al., "Interactions of synthetic peptide analogs of the class A amphipathic helix with lipids. Evidence for the snorkel hypothesis," J Biol Chem 269(10):7185-91 (1994).

Mishra et al., "Effect of the arrangement of tandem repeating units of class A amphipathic alpha-helixes on lipid interaction," J Biol Chem 270(4):1602-11 (1995).

Nedelec et al., "Comparative study of myelin proteolipid apoprotein solvation by multilayer membranes of synthetic DPPC and biological lipid extract from bovine brain. An FT-IR investigation," Biochimie 71(1):145-51 (1989).

Palgunachari et al., "Only the two end helices of eight tandem amphipathic helical domains of human apo A-I have significant lipid affinity. Implications for HDL assembly," Arterioscler Thromb Vasc Biol 16(2):328-38 (1996).

Paszty et al., "Apolipoprotein AI transgene corrects apolipoprotein E deficiency-induced atherosclerosis in mice," J Clin Invest 94(2):899-903 (1994).

Plump et al., "Human apolipoprotein A-I gene expression increases high density lipoprotein and suppresses atherosclerosis in the apolipoprotein E-deficient mouse," Proc Natl Acad Sci U S A 91(20):9607-11 (1994).

Ponsin et al., "In vitro binding of synthetic acylated lipid-associating peptides to high-density lipoproteins: effect of hydrophobicity," Biochemistry 23(22):5337-42 (1984).

Ponsin et al., "Lipid-peptide association and activation of lecithin:cholesterol acyltransferase. Effect of alpha-helicity," J Biol Chem 261(20):9202-5 (1986).

Pownall et al., "Activation of lecithin:cholesterol acyltransferase by a synthetic model lipid-associating peptide," Proc Natl Acad Sci U S A 77(6):3154-8 (1980).

Rogers et al., "Truncation of the amino terminus of human apolipoprotein A-I substantially alters only the lipid-free conformation," Biochemistry 36(2):288-300 (1997).

Rosseneu et al., "Physiological significance of apolipoprotein mutants," FASEB J 9(9):768-76 (1995).

Rubin et al., "Inhibition of early atherogenesis in transgenic mice by human apolipoprotein AI," Nature 353(6341):265-7 (1991).

Schnolzer et al., "Constructing proteins by dovetailing unprotected synthetic peptides: backbone-engineered HIV protease," Science 256(5054):221-5 (1992).

Schultz et al., "Protein composition determines the anti-atherogenic properties of HDL in transgenic mice," Nature 365(6448):762-4 (1993).

Segrest et al., "A molecular theory of lipid-protein interactions in the plasma lipoproteins," FEBS Lett 38(3):247-58 (1974).

Segrest et al., "Molecular packing of high density lipoproteins: a postulated functional role," FEBS Lett 69(1):111-5 (1976).

Segrest et al., "Studies of synthetic peptide analogs of the amphipathic helix. Competitive displacement of exchangeable apolipoproteins from native lipoproteins," J Biol Chem 258(4):2290-5 (1983).

Segrest et al., "Amphipathic helix motif: classes and properties," Proteins 8(2):103-17 (1990).

Segrest et al., "The amphipathic helix in the exchangeable apolipoproteins: a review of secondary structure and function," J Lipid Res 33(2):141-66 (1992).

Segrest et al., "The amphipathic alpha helix: a multifunctional structural motif in plasma apolipoproteins," Adv Protein Chem 45:303-69 (1994).

Sorci-Thomas et al., "Apolipoprotein A-I domains involved in lecithin-cholesterol acyltransferase activation. Structure:function relationships," J Biol Chem 268(28):21403-9 (1993).

Sorci-Thomas et al., "Alteration in apolipoprotein A-I 22-mer repeat order results in a decrease in lecithin:cholesterol acyltransferase reactivity," J Biol Chem 272(11):7278-84 (1997).

Sparks et al., "Effect of the cholesterol content of reconstituted LpA-I on lecithin:cholesterol acyltransferase activity," J Biol Chem 270(10):5151-7 (1995).

Sparrow et al., "Phospholipid binding studies with synthetic apolipoprotein fragments," Ann N Y Acad Sci 348:187 (1980).

Sparrow et al., "Apolipoprotein/lipid interactions: studies with synthetic polypeptides," CRC Crit Rev Biochem 13(1):87-107 (1982).

Spuhler et al., "Binding of apolipoprotein A-I model peptides to lipid bilayers. Measurement of binding isotherms and peptide-lipid headgroup interactions," J Biol Chem 269(39):23904-10 (1994).

Tam, "Synthetic peptide vaccine design: synthesis and properties of a high-density multiple antigenic peptide system," Proc Natl Acad Sci U S A 85(15):5409-13 (1988).

Tytler et al., "Reciprocal effects of apolipoprotein and lytic peptide analogs on membranes. Cross-sectional molecular shapes of amphipathic alpha helixes control membrane stability," J Biol Chem 268(29):22112-8 (1993).

Vanloo et al., "LCAT activation properties of apo A-I CNBr fragments and conversion of discoidal complexes into spherical particles," Biochim Biophys Acta 1128(2-3):258-66 (1992).

Venkatachalapathi et al., "Effect of end group blockage on the properties of a class A amphipathic helical peptide," Proteins 15(4):349-59 (1993).

Wang et al., "Conformation of human serum apolipoprotein A-I(166-185) in the presence of sodium dodecyl sulfate or dodecylphosphocholine by 1H-NMR and CD. Evidence for specific peptide-SDS interactions," Biochim Biophys Acta 1301(3):174-84 (1996).

Wilmot et al., "Analysis and prediction of the different types of beta-turn in proteins," J Mol Biol 203(1):221-32 (1988).

Yancey et al., "Efflux of cellular cholesterol and phospholipid to lipid-free apolipoproteins and class A amphipathic peptides," Biochemistry 34(24):7955-65 (1995).

Yokoyama et al., "The mechanism of activation of lecithin:cholesterol acyltransferase by apolipoprotein A-I and an amphiphilic peptide," J Biol Chem 255(15):7333-9 (1980).

Cox et al., "The interaction of calmodulin with amphiphilic peptides," J Biol Chem 260(4):2527-34 (1985).

Ameli et al, "Recombinant apolipoprotein A-I Milano reduces intimal thickening after balloon injury in hypercholesterolemic rabbits," *Circulation*; 90;1935-1941 (1993).

Anantharamaiah et al, "Use of synthetic peptide analogues to localize lecithin:cholesterol acyltransferase activating domain in apolipoprotein A-I," Arterioscler Thromb Vasc Biol; 10;95-105 (1990).

Cowell et al, "A Randomized Trial of Intensive Lipid-Lowering Therapy in Calcific Aortic Stenosis," N Engl J Med. Jun. 9 352(23) 2389-97 (2005).

Drolet et al, "Experimental Aortic Valve Stenosis in Rabbits," J Am Coll Cardiol Apr. 2 41(7) 1211-7 (2003).

Freeman et al, "Spectrum of Calcific Aortic Valve Disease: Pathogenesis, Disease Progression, and Treatment Strategies," Circulation, Jun. 21, 111(24), 3316-2 (2005).

Navab et al, "Apolipoprotein A-I Mimetic Peptides,"Art Thr Vasc Biol, Jul. 25(7), 1325-31 (2005).

Nissen et al, "Effect of Recombinant ApoA-I Milano on Coronary Atherosclerosis in Patients With Acute Coronary Syndromes," JAMA, 290(17), 2292-2300 (2003).

Nissen et al, "Effect of Very High-Intensity Statin Therapy on Regression of Coronary Atherosclerosis," JAMA, Apr. 5, 295(13), 1556-65 (2006).

Shah et al, High-Dose Recombinant Apolipoprotein A-I Milano Mobilizes Tissue Cholesterol and et al, Circulation, Jun. 26, 103(25), 3047-50 (2001).

Tardif et al, "Effects of Reconstituted High-Density Lipoprotein Infusions on Coronary Atherosclerosis," JAMA, Apr. 18, 297(15), 1675-82 (2007).

Kaul et al, "Intramural Delivery of Recombinant Apolipoprotein A-I Milano/Phospholipid et al," Circulation, 107, 2551-2554 (2003).

* cited by examiner

METHOD FOR THE TREATMENT OF VALVULAR DISEASE

This application is a U.S. national stage of International Application No. PCT/CA2007/000895 filed May 23, 2007, which claims the benefit of U.S. Provisional Patent Application Ser. No. 60/809,850 filed Jun. 1, 2006, the disclosure of which is hereby incorporated by reference in its entirety.

FIELD OF THE INVENTION

The present invention relates to the general field of medical methods and compounds and is particularly concerned with a method and compound for the treatment of valvular disease.

BACKGROUND OF THE INVENTION

The function of the heart is to supply the energy required for the circulation of blood in the cardiovascular system. Blood flow through all organs is passive and occurs only because arterial pressure is kept higher than venous pressure by the pumping action of the heart. The right heart pump provides the energy necessary to move blood through the pulmonary vessels and the left heart pump provides the energy that causes flow through the systemic organs.

Venous blood returns from the systemic organs to the right atrium via the superior and inferior venae cavae. It passes through the tricuspid valve into the right ventricle and from there is pumped through the pulmonic valve into the pulmonary circulation via the pulmonary arteries. Oxygenated pulmonary venous blood flows in pulmonary veins to the left atrium and passes through the mitral valve into the left ventricle. From there, it is pumped through the aortic valve into the aorta to be distributed to the systemic organs.

Hence, in its normal operation, the left ventricle of the heart pumps oxygen-rich blood to arteries in the vasculature of the body through the aorta. As the heart pumps, the aortic valve, which is located between the left ventricle and the aorta, opens and closes to control the direction of blood flow. More specifically, during heartbeat or systole, the aortic valve is opened to allow blood to flow from the left ventricle into the aorta. Between heartbeats, or during diastole, however, the aortic valve closes to form a tight seal that prevents blood from leaking back into the ventricle.

The valves are structurally designed to allow flow in only one direction and passively open and close in response to the direction of the pressure differences across them. Typically, the aortic valve is composed of three fibrous leaflets or cusps. The leaflets are forced open against the walls of the aorta during ventricular ejection of blood but fall back during diastole, their free edges coapting to prevent blood from returning into the heart.

The aortic wall behind each aortic valve cusp bulges outward, forming three structures known as sinuses of Valsalva. The two most anterior valvular aortic cusps are known as the left and right coronary cusps because of the origin of the left and right coronary arteries from the respective sinuses of Valsalva and the remaining valvular posterior cusp is known as the non-coronary cusp.

For any of several reasons, it can happen that the aortic valve is somehow damaged and may become stenosed. When this happens, the aortic valve does not open to its normal extent and the flow of blood from the heart into the aorta is hindered. This leads to a heart condition that is commonly known as aortic valve stenosis.

Common etiologies for aortic valve stenosis include congenital abnormality, rheumatic fever or degeneration with calcification in the aging patient. A bicuspid valve is the most common congenital abnormality, and often a raphe in one of the cusps indicates failure of the commissure to develop. Rarely, a unicuspid or quadricuspid valve can be present at birth. Although the bicuspid valve may not be initially stenotic, fibrosis and thickening lead eventually to reduced orifice size with calcification. Indeed, mechanical sheer stress typically leads to calcific injury.

Rheumatic fever scars the leaflet margins, and eventually the commissures fuse and calcify. More than 50% of adults with aortic stenosis are found to have a bicuspid valve, but fibrosis and calcification may make it difficult to determine whether the valve is bicuspid or tricuspid.

In the aging patient with degenerative aortic valve stenosis, calcium deposits usually develop at the sinuses and annulus, whereas the margins of the leaflets often remain free of calcifications.

Currently, there are many proposed theories for the cellular pathophysiology of aortic valve stenosis. Such theories include cardiovascular risk factors initiating a response to injury, mechanical sheer stress, auto-immune phenomena causing degeneration, chronically raised stroke volume and altered calcium metabolism (such as found in renal failure, Paget's disease, etc.).

Regardless of its etiology, aortic stenosis produces an increase in systolic left ventricular pressure. Systolic hypertension in the ventricular chamber is compensated by concentric hypertrophy of the myocardial wall, allowing the wall stress to remain normal. The less compliant, thickened left ventricle becomes more dependent on the atrial contribution to diastolic filling, such that left ventricular performance can deteriorate when atrial contraction is lost, for example during atrial fibrillation or atrial-ventricular dissociation. The abnormal relaxation and increased stiffness of the thickened left ventricle during diastole also result in diastolic dysfunction and elevations of left ventricular and left atrial diastolic pressures.

Myocardial failure can eventually develop from chronic severe valvular obstruction and depression of the contractile state. Left ventricular dilatation can also occur in some patients. Myocardial oxygen consumption remains high owing to elevation of systolic pressure in the left ventricle and increase in left ventricular mass. In addition, the increased left ventricular diastolic pressure reduces the pressure gradient necessary for myocardial perfusion. Thus, significant aortic stenosis creates conditions in which high myocardial oxygen demands are inadequately supported by reduced oxygen supply, which leads to subendocardial ischemia.

Eventually, with a decline in the inotropic state of the myocardium, the ejection fraction is decreased to below the normal range (with or without associated dilatation of the left ventricle). Further elevation of the left ventricular end diastolic pressure (secondary to diastolic dysfunction with or without systolic dysfunction) results in pulmonary venous hypertension. The increased myocardial oxygen demands in aortic stenosis with the underperfused subendocardial myocardium can produce angina pectoris, arrhythmias, and even sudden death.

The development of any of the cardinal symptoms in the setting of severe aortic stenosis indicates substantial mortality risk and is an indication for surgical therapy. The average life expectancy after symptom onset is 2-3 years, less if the symptoms are due to heart failure. Because symptoms, and perhaps sudden death, often accompany physical exertion, vigorous activities and competitive sports should be avoided by patients with aortic stenosis, even if it is only mild to moderate in severity. Hence, aortic stenosis is associated not only with high mortality but also with substantial morbidity.

Calcific aortic stenosis accounts for a large percentage of aortic stenosis cases. The condition is characterized by the build-up of calcified nodules on the upper or superior surface of the aortic valve leaflets. These nodules decrease the flexibility of the leaflets, thereby limiting their mobility and capacity to fully open.

Three techniques have been employed to correct aortic stenosis, namely valve replacement, intra-operative decalcification or debridement or the heart valve and balloon valvuloplasty.

Valve replacement, during open-heart surgery, is currently the standard therapy for symptomatic aortic stenosis. Ten-year survival rates for isolated aortic valve replacement are relatively good, even in elderly patients. However, this technique requires the patient to be healthy enough to undergo sternotomy (chest opening) and open heart surgery. The operative mortality for this procedure, particularly in the elderly, is relatively large.

There are two types of prosthetic heart valves, namely mechanical valves that are composed of only materials that are not derived from living organisms and bio-prosthetic valves that are composed in whole or in part of biological material. Mechanical valves currently in use have a ball-cage construction, a tilted disc construction (1 or 2 discs) or a hinged leaflet construction.

Bio-prosthetic valves generally comprise a supporting stent and a plurality of leaflets. The leaflets are generally composed of biological material, while the stent, when present, generally comprises non-biological material, at least in part. The biological material of the leaflets can be autologous tissues such as pericardium, fascia lata or cardiac valves. Alternatively, this material can be derived from homologous tissue such as non-autologous human tissue for human implantation or can be xenogeneic.

Each type of prosthetic heart valve has advantages and disadvantages. Mechanical heart valves are durable and, hence, more likely to result in long-lasting function but require careful chronic anticoagulation because of thrombo-embolic risk. Chronic anticoagulation therapy, however, carries with it a risk of haemorrhage similar in incidence to that of the residual risk for thrombotic events.

Bio-prosthetic valves initially approximate the haemodynamic properties of the natural valve. They carry a smaller risk of complications secondary to thrombus than do mechanical valves. Such valves, however, carry a significantly higher risk of calcification than mechanical valves. Since treatment of a functionally compromised bio-prosthetic heart valve frequently requires replacement with a new valve (and hence a second open-heart surgery), limitations on the useful life expectancy of a bio-prosthetic heart valve are both a serious medical problem for the patient and a financial drain on the medical system.

Furthermore, all prosthetic heart valves are somewhat stenotic. Prosthetic dysfunction secondary to thrombosis or calcification can lead to increased obstruction or the development of regurgitation. Regurgitation can also result from a perivalvular leak, that is a leak in the area of the sewing ring of the valve. Turbulence associated with valve dysfunction can cause haemolysis and anemia. Even normally functioning prosthetic valves can cause haemolysis in some patients.

Endocarditis is another potential and major complication in patients with prosthetic heart valves. Antibiotic prophylaxis has to be administered prior to dental, gastrointestinal and genito-urinary surgery and other procedures associated with bacteraemia.

Furthermore, some patients have aortic dimensions that are not large enough to easily accommodate conventional replacement valves. Hence, there is a significant number of patients for whom valve replacement is impossible, impractical, or undesirable.

Intra-operative mechanical debridement or decalcification of the aortic valve was used for many years prior to the advent of mechanical replacement valves. In this technique, the aorta is entered surgically but, rather than replace the valve manually, the surgeon removes the calcified deposits, using suitable surgical tools. Recently, ultrasonic debridement has also been demonstrated to be effective to remove calcific deposits. Nevertheless, this technique still requires the patient to be healthy enough to survive and recuperate from thoracic surgery, and involves all the costs and risks attendant with such surgery.

A third technique for correcting aortic stenosis involves percutaneous balloon aortic valvuloplasty. In this procedure, an inflatable balloon catheter is advanced to the aortic valve and inflated to compress and fracture the calcified nodules in an attempt to increase leaflet mobility. Although this procedure eliminates many of the risks and disadvantages attendant with the preceding two techniques, re-stenosis is very common within one year, limiting the usefulness of the technique to temporarily mitigating symptoms for those patients who are poor surgical candidates or refuse surgery.

Hence, there exists a need for a non-surgical treatment of aortic valve stenosis and other valvular diseases.

The present invention differs significantly from the prior art and current trends by providing a method for not only preventing the progression of aortic stenosis but also for reducing the degree of stenosis using a reverse lipid transport agonist.

An object of the present invention is therefore to provide a novel non-surgical treatment of valvular disease.

SUMMARY OF THE INVENTION

In a broad aspect, the invention provides a method for preventing or treating a valvular stenosis in a subject, the method comprising administering to a subject in need thereof a therapeutically effective amount of a reverse lipid transport agonist. For example, the lipid transport agonist is a reverse cholesterol transport agonist.

In some embodiments of the invention, the valvular stenosis is an aortic valve stenosis, a calcific valve stenosis, or any other valvular stenosis.

In some embodiments of the invention, the reverse lipid transport agonist is selected from the group consisting of: an HDL, a peptide with HDL-like physiological effects, a peptide with HDL-like physiological effects complexed to a lipid, an HDL-mimetic agents, a CETP modulator, an SRB1 modulators, an LXR/RXR agonist, an ABCA1 agonists, a PPAR agonist and an Apolipoprotein A-I (ApoA-1) mimetic peptide/phospholipid complex.

In this latter case, administering the ApoA-1 mimetic peptide/phospholipid complex may include injecting the ApoA-1 mimetic peptide/phospholipid complex in the subject. Examples of dosages in this case are of from about 1 µg to about 10 g per kg body weight of the subject, about 1 mg to about 0.5 g per kg body weight of the subject, and about 25 mg per kg body weight of the subject.

For example, the ApoA-1 mimetic peptide has the sequence of SEQ ID NO: 1 found herein below, and the ApoA-1 mimetic peptide may be complexed with egg sphingomyelin and 1,2-dipalmitoyl-sn-glycero-3-phosphocholine (DPPC).

In some embodiments, the subject is a mammal, for example a human.

In another broad aspect, the invention provides a method for preventing or treating a valvular calcification in a subject, the method comprising administering to a subject in need thereof a therapeutically effective amount of a reverse lipid transport agonist.

In yet another broad aspect, the invention provides a method for controlling a valvular stenosis in a subject, the method comprising increasing reverse cholesterol transport in a subject in need thereof.

In yet another broad aspect, the invention provides a method for preventing or reversing valvular stenosis, the method comprising administering to a patient in need thereof a reverse lipid transport agonist.

In yet another broad aspect, the invention provides a method for controlling a valvular stenosis in a subject, the method comprising administering to a subject in need thereof a therapeutically effective amount of a reverse lipid transport agonist.

For example, controlling the valvular stenosis may include reducing a rate of progression of the valvular stenosis, or reversing, at least in part, the valvular stenosis.

In yet another broad aspect, the invention provides the use of a reverse lipid transport agonist for controlling valvular stenosis in a subject.

In yet another broad aspect, the invention provides the use of a reverse lipid transport agonist for the manufacture of a pharmaceutical composition of matter for controlling valvular stenosis in a subject In a variant, the method comprises the administration of a therapeutically effective amount of a compound, referred to hereinafter as compound A, that mimics biologic properties of Apolipoprotein A-1 (ApoA-1). Compound A and other suitable compounds are described in U.S. Pat. Nos. 6,287,590, issued Sep. 11, 2001, and 6,506,799, issued Jan. 14, 2003, which are hereby incorporated by reference in their entirety. Indeed, it is believed that in view of current knowledge regarding the action of the compounds and molecules described in these Patents, results similar to those presented herein are obtainable with these compounds and molecules.

Advantageously, the proposed method replaces relatively invasive or relatively ineffective existing treatments for valvular diseases. Also, in addition to slowing the progression of valvular disease, the proposed method also reverses valvular stenosis. Accordingly, the proposed treatment not only has a potential to slow down or stop the progression of aortic valve stenosis and other valvular diseases, but also to cause the regression of aortic valve stenosis and other valvular diseases.

Aortic valve stenosis (AVS) is the most common valvular heart disease, and standard curative therapy remains open-heart surgical valve replacement. To determine if reverse lipid transport agonists have a potential to prevent or treat AVS, ApoA-1 mimetic peptide infusions were tested to determine if they could induce regression of AVS. To that effect, fifteen New-Zealand White male rabbits received a cholesterol-enriched diet and vitamin $D_2$ until significant AVS was detected by echocardiography. Animals were then randomized to receive saline (control group, n=8) or an ApoA-1 mimetic peptide (treated group, n=7), 3 times per week for 2 weeks. Serial echocardiograms and post mortem valve histology were performed. Aortic valve area improved significantly in the treated group compared to controls after 7 (21.9±3.6 mm$^2$ vs. 19.6±1.8 mm$^2$, P=0.019) (increases of 14.2% and 3.9%), 10 (23.0±4.1 mm$^2$ vs. 20.3±2.4 mm$^2$, P=0.006) (19.8% vs. 7.6%) and 14 days of treatment (23.8±3.1 mm$^2$ vs. 21.3±2.4 mm$^2$, P=0.012) (24.6% vs. 12.9%). Aortic valve thickness decreased by 21% within 14 days of treatment in the treated group (0.094±0.034 cm vs. 0.075±0.033 cm) whereas it was unchanged in controls (P=0.0006). Lesion extent at the base of valve leaflets and sinuses of Valsalva was smaller in the treated compared to control group (52.8±12.5% vs. 66.7±9.9%, P=0.032). A strong trend towards decreased calcification areas was also observed (1.6±2.0% vs. 6.9±6.7%, P=0.063). Therefore, infusions of ApoA-1 mimetic peptide lead to regression of experimental AVS.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
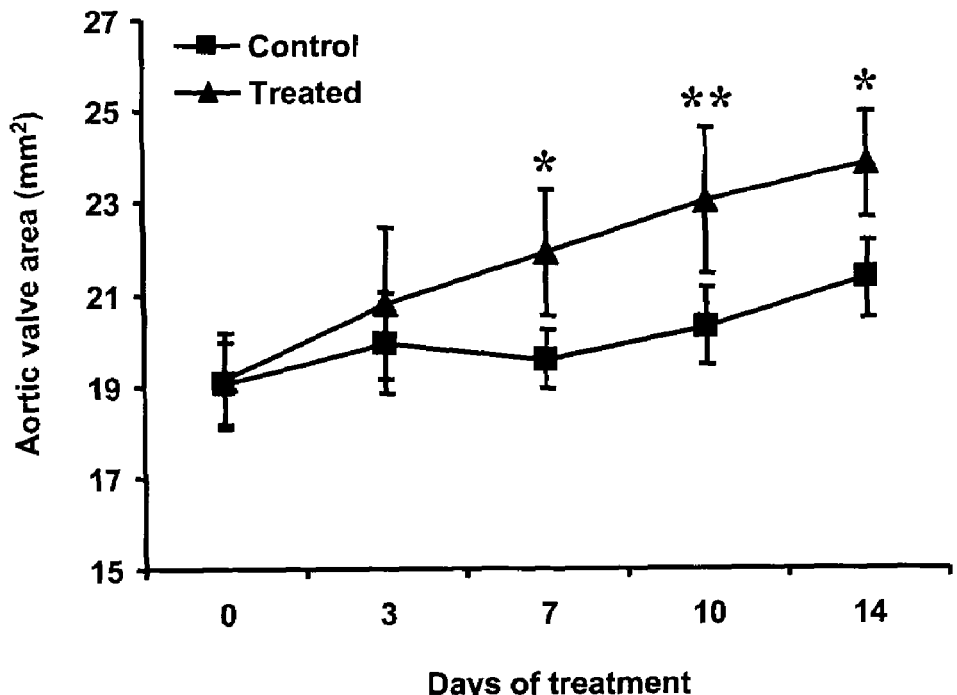
FIG. 1 illustrates aortic valve area values obtained through echocardiographic measurements obtained during the ApoA-1 mimetic peptide treatment period. Day "0" corresponds to the end of cholesterol plus vitamin $D_2$ diet and the beginning of ApoA-1 mimetic peptide treatment period, *P<0.05; **P<0.01.

The present description refers to many public documents, the contents of which are hereby incorporated by reference in their entirety. Histopathological, experimental and clinical data suggest that calcific aortic valve stenosis (AVS) is an active disease process with lipoprotein deposition, inflammation and active leaflet calcification (1). Although there are some similarities between AVS and atherosclerosis, their pathophysiology and treatments differ significantly. In terms of pathophysiology, a bicuspid aortic valve is present and contributes to the disease in approximately half the patients with AVS, whereas atherosclerosis is not due to a structural congenital abnormality. Rheumatic heart disease can also lead to AVS, while it has not been linked to atherosclerosis. Calcific AVS of the elderly, the most frequent type in the western countries, often leads to isolated aortic valve replacement without the need for associated coronary bypass surgery. In terms of medical treatments, statins have been shown to be protective in patients with coronary disease and to halt progression or induce regression of atherosclerosis (3); in contrast, the progression of AVS was not prevented by intensive statin therapy in a recent randomized clinical trial (4). Similarly, angiotensin-converting enzyme inhibitors have been shown to be cardioprotective in several large-scale clinical trials but have failed to slow progression of AVS. In summary, atherosclerosis and AVS are distinct diseases, affecting different patient populations.

There is an inverse relationship between plasma levels of HDL-cholesterol and coronary artery disease. Studies in animals with experimental atherosclerosis have demonstrated that ApoA-1 Milano/phospholipid complexes rapidly mobilize cholesterol and thereby reduce atherosclerotic plaque burden (5, 6). In addition, two clinical studies have suggested that infusions of reconstituted HDL could induce rapid improvement of coronary atherosclerosis (7, 8). We have hypothesized that an HDL-based therapy may also induce regression of AVS. If this could be achieved safely, medical treatment of AVS and its regression may transform our clinical approach of this frequent disease. Apolipoprotein A-I (ApoA-1) is a structural component of HDL that mediates many of its beneficial effects including enhanced reverse cholesterol transport (9). The peptide used in our study is capable of forming an amphipathic alpha-helix in the presence of lipids, as is the case for ApoA-1 (10, 11). We have therefore tested the ability of this ApoA-1 mimetic peptide complexed with phospholipids, mimicking nascent HDL, to induce regression of calcific AVS in a previously described rabbit model (12).

As is well known, the main function of lipoproteins in plasma is to transport lipids, such as cholesterol and triglycerides. For transport in plasma, cholesterol, normally as cholesterol esters, and the triglycerides are included into lipoprotein particles in which they form a hydrophobic core. The core is surrounded by a surface coat containing phospholipids, unesterified cholesterol and proteins called apolipoproteins. The latter are responsible for the lipid transport and, in addition, some may interact with many of the enzymes involved in lipid metabolism. To date, at least 10 apolipoproteins have been identified, namely: A-1, A-2, A-4, B-48, B-100, C-I, C-II, C-III, D and E.

We have hypothesized that a strategy directed to increasing the efficiency of the reverse lipid transport mechanism through the use of a suitable compound is a possible approach in the treatment of valvular disease. There is also a possibility that calcific deposits might be removed, thereby effectively curing valvular stenosis.

The compound used to test this hypothesis, hereinafter referred to as Compound A, is a lipoprotein that mimics biologic properties of apolipoprotein A-I (ApoA-1). This type of compound, an Apo A-I mimetic or agonist, is described in further detail in U.S. Pat. No. 6,376,464 titled "Lipid complexes of APO A-1 agonist compounds," issued to Dasseux et al. on Apr. 23, 2002. This document is hereby incorporated by reference in its entirety.

Briefly, these compounds include peptides, or analogues thereof, which are capable of forming amphipathic alpha-helices in the presence of lipids and which mimic the activity of ApoA-1. They are therefore referred-to as ApoA-1 agonists. The agonists have as their main feature a "core" peptide composed of 15 to 29 amino acid residues, preferably 22 amino acid residues, or an analogue thereof wherein at least one amide linkage in the peptide is replaced with a substituted amide, an isostere of an amide or an amide mimetic.

These ApoA-1 agonists are based, in part, on the discovery that altering certain amino acid residues in the primary sequence of the 22-mer consensus sequence disclosed in Venkatachalapathi et al., Mol. Conformation and Biol. Interactions, Indian Acad. Sci. B: 585-596 (PVLDEFREKLNEE-LEALKQKLK; hereinafter "Segrest's consensus 22-mer" or "consensus 22-mer") (SEQ ID NO:2) that were thought to be critical for activity, yields synthetic peptides which exhibit activities that approach, or in some embodiments even exceed, the activity of native ApoA-1. It was discovered that replacing three charged amino acid residues in Segrest's consensus 22-mer peptide (Glu-5, Lys-9 and Glu-13) with a hydrophobic Leu residue provides peptides that mimic the structural and functional properties of ApoA-1 to a degree that was unprecedented in the art.

Compound A comprises a peptide having the sequence:

```
                                           (SEQ ID NO: 1)
H-Pro-Val-Leu-Asp-Leu-Phe-Arg-Glu-Leu-Leu-Asn-Glu-
Leu-Leu-Glu-Ala-Leu-Lys-Gln-Lys-Leu-Lys-OH
``` and was synthesized by Polypeptide Laboratories (Torrance, Calif., USA). Purity assessed by high performance liquid chromatography and mass spectral analysis was greater than 98%. The peptide was complexed with egg sphingomyelin and 1,2-dipalmitoyl-sn-glycero-3-phosphocholine (DPPC) (Avanti Polar Lipids) (10) in a 1:1:1 weight ratio by mixing the components in saline and performing multiple heating and cooling cycles until the solution appeared perfectly clear. The solution containing the complexes was lyophilized in aliquots for long-term storage. Fresh solution was reconstituted every week under sterile conditions and kept at 4° C. Biological activity of the complex was tested in rats for its ability to mobilize cholesterol and to raise HDL-cholesterol in blood following an intravenous injection of the peptide (data not shown).

Based on their known biological activity and structures, it is believed that other compounds, such as the compounds presented in the above-mentioned U.S. Pat. No. 6,376,464, will show effects similar to Compound A.

Suitable compounds disclosed in U.S. Pat. No. 6,376,464 include, but are not limited to, peptides of the following Formula (I)

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22}$$

and pharmaceutically acceptable salts thereof, wherein:
$X_1$ is Pro (P), Ala (A), Gly (G), Gln (Q), Asn (N), Asp (D) or D-Pro (p);
$X_2$ is an aliphatic amino acid;
$X_3$ is Leu (L) or Phe (F);
$X_4$ is an acidic amino acid;
$X_5$ is Leu (L) or Phe (F);
$X_6$ is Leu (L) or Phe (F);
$X_7$ is a hydrophilic amino acid;
$X_8$ is an acidic or a basic amino acid;
$X_9$ is Leu (L) or Gly (G);
$X_{10}$ is Leu (L), Trp (W) or Gly (G);
$X_{11}$ is a hydrophilic amino acid;
$X_{12}$ is a hydrophilic amino acid;
$X_{13}$ is Gly (G) or an aliphatic amino acid;
$X_{14}$ is Leu (L), Trp (W), Gly (G) or Nal;
$X_{15}$ is a hydrophilic amino acid;
$X_{16}$ is a hydrophobic amino acid;
$X_{17}$ is a hydrophobic amino acid;
$X_{18}$ is Gln (Q), Asn (N) or a basic amino acid;
$X_{19}$ is Gln (Q), Asn (N) or a basic amino acid;
$X_{20}$ is a basic amino acid;
$X_{21}$ is an aliphatic amino acid; and
$X_{22}$ is a basic amino acid.

In one embodiment, the compound of Formula (I) is a 22 amino acid residue peptide in which:
$X_1$ is Pro (P), Gly (G), Ala (A), Gln (Q), Asn (N), Asp (D) or D-Pro (p);
$X_2$ is Ala (A), Val (V) or Leu (L);

$X_4$ is Asp (D) or Glu (E);
$X_7$ is Lys (K), Arg (R), Orn, Asn (N) or Glu (E);
$X_8$ is Asp (D), Arg (R) or Glu (E);
$X_{11}$ is Asn (N), Gln (Q), Glu (E) or Arg (R);
$X_{12}$ is Asp (D), Glu (E) or Asn (N);
$X_{13}$ is Leu (L), Gly (G) or Aib;
$X_{15}$ is Asp (D), Glu (E), Gln (Q) or Lys (K);
$X_{16}$ is Ala (A), Trp (W), Gly (G), Leu (L), Phe (F) or NaI;
$X_{17}$ is Leu (L), Gly (G) or NaI;
$X_{18}$ is Lys (K), Orn, Gln (Q) or Asn (N);
$X_{19}$ is Lys (K), Orn, Gln (Q) or Asn (N);
$X_{20}$ is Lys (K) or Orn;
$X_{21}$ is Leu (L); and/or
$X_{22}$ is Lys (K) or Orn.

In another embodiment, the compound of Formula (I) is a 22 amino acid residue peptide in which:
$X_2$ is Val (V);
$X_3$ is Leu (L);
$X_5$ is Leu (L);
$X_6$ is Phe (F);
$X_7$ is Arg (R) or Lys (K);
$X_8$ is Glu (E);
$X_9$ is Leu (L);
$X_{10}$ is Leu (L);
$X_{11}$ is Asn (N) or Glu (Q);
$X_{12}$ is Glu (E); and/or
$X_{15}$ is Glu (E).

In another embodiment, the compound of Formula (I) is a 22 amino acid residue peptide in which:
$X_1$ is Pro (P), Gly (G) or D-Pro (p);
$X_2$ is Val (V);
$X_3$ is Leu (L);
$X_4$ is Asp (D) or Glu (E);
$X_5$ is L (Leu) or Phe (F);
$X_6$ is Phe (F);
$X_7$ is Arg (R);
$X_8$ is Glu (E);
$X_9$ is Leu (L);
$X_{10}$ is Leu (L) or Trp (W);
$X_{11}$ is Asn (N);
$X_{12}$ is Glu (E);
$X_{13}$ is Gly (G);
$X_{14}$ is Leu (L);
$X_{15}$ is Glu (E);
$X_{16}$ is Ala (A) or Trp (W);
$X_{17}$ is Leu (L) or NaI;
$X_{18}$ is Lys (K) or Orn;
$X_{19}$ is Gln (Q);
$X_{20}$ is Lys (K) or Orn;
$X_{21}$ is Leu (L); and
$X_{22}$ is Lys (K) or Orn.

In another embodiment, the compound of Formula (I) is a 22 amino acid residue peptide in which:
$X_1$ is Pro (P), Gly (G), Ala (A) or D-Pro (p);
$X_2$ is Val (V) or Leu (L);
$X_3$ is Leu (L);
$X_4$ is Asp (D) or Glu (E);
$X_5$ is Leu (L) or Phe (F);
$X_6$ is Leu (L) or Phe (F);
$X_7$ is Arg (R) or Lys (K);
$X_8$ is Glu (E);
$X_9$ is Leu (L);
$X_{10}$ is Leu (L) or Trp (W);
$X_{11}$ is Asn (N) or Gln (Q);
$X_{12}$ is Glu (E);
$X_{13}$ is Leu (L) or Aib;
$X_{14}$ is Leu (L), Trp (W) or NaI;
$X_{15}$ is Glu (E);
$X_{16}$ is Ala (A), Leu (L), Trp (W) or NaI;
$X_{17}$ is Leu (L) or NaI;
one of $X_{18}$ or $X_{19}$ is Gln (Q) and the other is Lys (K) or Orn;
$X_{20}$ is Lys (K) or Orn;
$X_{21}$ is Leu (L); and
$X_{22}$ is Lys (K) or Orn.

In another embodiment, the compound of Formula (I) is a 22 amino acid residue peptide in which:
$X_2$ is Val (V);
$X_4$ is Asp (D);
$X_5$ is Leu (L);
$X_6$ is Phe (F);
$X_7$ is Arg R);
$X_{10}$ is Leu (L);
$X_{11}$ is Asn (N);
$X_{13}$ is Leu (L);
$X_{14}$ is Leu (L);
$X_{16}$ is Ala (A);
$X_{17}$ is Leu (L);
$X_{18}$ is Lys (K);
$X_{19}$ is Gln (Q);
$X_{20}$ is Lys (K) and/or
$X_{22}$ is Lys (K).

Compounds of Formula (I) include, for example, peptides of SEQ ID NOS. 3-51, as set forth below.
PVLDLFRELLNELLEZLKQKLK (SEQ ID NO:3);
GVLDLFRELLNELLEALKQKLKK (SEQ ID NO:4);
PVLDLFRELLNELLEWLKQKLK (SEQ ID NO:5);
PVLDLFRELLNELLEALKQKLK (SEQ ID NO:6);
pVLDLFRELLNELLEALKQKLKK (SEQ ID NO:7);
PVLDLFRELLNEXLEALKQKLK (SEQ ID NO:8);
PVLDLFKELLNELLEALKQKLK (SEQ ID NO:9);
PVLDLFRELLNEGLEALKQKLK (SEQ ID NO:10);
PVLDLFRELGNELLEALKQKLK (SEQ ID NO:11);
PVLDLFRELLNELLEAZKQKLK (SEQ ID NO:12);
PVLDLFKELLQELLEALKQKLK (SEQ ID NO:13);
PVLDLFRELLNELLEAGKQKLK (SEQ ID NO:14);
GVLDLFRELLNEGLEALKQKLK (SEQ ID NO:15);
PVLDLFRELLNELLEALOQOLO (SEQ ID NO:16);
PVLDLFRELWNELLEALKQKLK (SEQ ID NO:17);
PVLDLRELLNELLEALKQKLK (SEQ ID NO:18);
PVLELFKELLQELLEALKQKLK (SEQ ID NO:19);
GVLDLFRELLNELLEALKQKLK (SEQ ID NO:20);
pVLDLFRELLNEGLEALKQKLK (SEQ ID NO:21);
PVLDLFREGLNELLEALKQKLK (SEQ ID NO:22);
pVLDLFRELLNELLEALKQKLK (SEQ ID NO:23);
PVLDLFRELLNELLEGLKQKLK (SEQ ID NO:24);
PLLELFKELLQELLEALKQKLK (SEQ ID NO:25);
PLLELFKELLQELLEALKQKLK (SEQ ID NO:26);
PVLDFFRELLNEXLEALKQKLK (SEQ ID NO:27);
PVLDLFRELLNELLELLKQKLK (SEQ ID NO:28);
PVLDLFRELLNELZEALKQKLK (SEQ ID NO:29);
PVLDLFRELLNELWEALKQKLK (SEQ ID NO:30);
AVLDLFRELLNELLEALKQKLK (SEQ ID NO:31);
QVLDLFRELLNELLEALKQKLK (SEQ ID NO:32);
PVLDLFOELLNELLEALOQOLO (SEQ ID NO:33);
NVLDLFRELLNELLEALKQKLK (SEQ ID NO:34);
PVLDLFRELLNELGEALKQKLK (SEQ ID NO:35);
PVLDLFRELLNELLELLKQKLK (SEQ ID NO:36);
PVLDLFRELLNELLEFLKQKLK (SEQ ID NO:37);
PVLELFNDLLRELLEALQKKLK (SEQ ID NO:38);
PVLELFNDLLRELLEALRQKLK (SEQ ID NO:39);
PVLELFKELLNELLDALRQKLK (SEQ ID NO:40);
PVLDLFRELLENNLLEALQKKLK (SEQ ID NO:41);
PVLELFERLLEDLLQALNKKLK (SEQ ID NO:42);
PVLELFERLLEDLLKALNQKLK (SEQ ID NO:43);

DVLDLFRELLNELLEALKQKLK (SEQ ID NO:44);
PALELFKDLLQELLEALKQKLK (SEQ ID NO:45);
PVLDLFRELLNEGLEAZKQKLK (SEQ ID NO:46);
PVLDLFRELLNEGLEWLKQKLK (SEQ ID NO:47);
PVLDLFRELWNEGLEALKQKLK (SEQ ID NO:48);
PVLDLFRELLNEGLEALOQOLO (SEQ ID NO:49);
PVLDLFRELLNEGLEALQKKLK (SEQ ID NO:50); and
PVLELFRELLNEGLEALKQKLK (SEQ ID NO:51).
wherein X is Aib; Z is NaI; and O is Orn.

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The abbreviations used for the D-enantiomers of the genetically encoded amino acids are lower-case equivalents of the one-letter symbols. For example, "R" designates L-arginine and "r" designates D-arginine.

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gin (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gin (Q) Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:1.25-142. Genetically encoded hydrophobic amino acids include Pro (P), Ile (I), Phe (F), Val (V), Leu (L), Trp (W), Met (M), Ala (A), Gly (G) and Tyr (Y).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "treating" or "treatment" of a state, disease, disorder or condition includes:
(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;
(2) inhibiting the state, disease, disorder or condition, i.e., arresting or reducing the development of the state, disease, disorder or condition or at least one clinical or subclinical symptom thereof; or
(3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

Pharmaceutical Compositions

The pharmaceutical composition of the present invention comprises at least one compound of the present invention and a pharmaceutically acceptable excipient (such as a pharmaceutically acceptable carrier or diluent). Preferably, the pharmaceutical composition comprises a therapeutically effective amount of the compound(s) of the present invention. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions of the present invention may be prepared by conventional techniques, e.g., as described in Remington: The Science and Practice of Pharmacy, 20th Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Example

A complex animal model of aortic valve stenosis has been developed in rabbits. The model resulted in aortic valve stenosis characterized by a calcification similar to what is observed in a clinical setting in humans.

Methods

Animals and Experiments

An animal model adapted from that described by Drolet et al. (12) was used. Fifteen male New-Zealand White rabbits (2.7-3.0 kg, aged 12-13 weeks) were fed with a 0.5% cholesterol-enriched diet (Harlan, Indianapolis, Ind.) plus vitamin $D_2$ (50000 UI per day; Sigma, Markham, Canada) in the drinking water until significant AVS, as defined by a decrease $\geq 10\%$ of aortic valve area (AVA) or of the transvalvular velocities ratio ($V_1/V_2$), could be detected by echocardiography (12.9±2.4 weeks).

The animals then returned to a standard diet (without vitamin $D_2$) to mimic cholesterol lowering and were randomly assigned to receive either saline (control group, n=8) or the ApoA-1 mimetic peptide (treated group, n=7). Rabbits were given injections through the marginal ear vein of saline or of the ApoA-1 mimetic peptide (25 mg/kg) complexed with phospholipids (Compound A), 3 times per week for 2 weeks. Echocardiograms were performed serially (see Echocardiography Methods) every 3 to 4 days throughout the randomized treatment period. Two days after their last infusion, the animals underwent a final echocardiogram and were sacrificed, and the aortic valves were harvested for histological analyses. Blood samples were obtained through the ear artery at baseline, prior to treatment and before sacrifice. Total cholesterol, HDL cholesterol, triglycerides and calcium levels were measured with an automated filter photometer system (Dimension RxL Max, Dade Behring, Ill.).

Animal care and procedures complied with the Canadian Council on Animal Care guidelines and were approved by the institutional ethics committee for animal research.

Echocardiography

Transthoracic echocardiographic studies were performed at baseline, on a weekly basis starting at 8 weeks of hypercholesterolemic diet until significant AVS developed, and then after 4, 7, 10 and 14 days of ApoA-1 mimetic peptide or saline control treatments. Studies were carried out with an S12 probe using a standard echocardiographic system (Sonos 5500, Philips Medical Imaging, MA). Intra-muscular injections of ketamine (45 mg/kg) and midazolam (0.75 mg/kg) were used for sedation.

Parasternal long and short-axis views of the aortic valve were recorded to assess leaflet morphology. Left ventricular outflow tract (LVOT) diameter was measured in a zoomed parasternal long-axis view, and LVOT cross-sectional area ($CSA_{LVOT}$) was calculated according to: $CSA_{LVOT}=\pi(D_{LVOT}/2)^2$. LVOT velocity (V1) and velocity time integral ($VTI_{LVOT}$) were obtained with pulsed-wave Doppler sampled proximal to the aortic valve in the apical 5-chamber view. Continuous wave (CW) Doppler interrogation across the aortic valve was used to obtain transvalvular maximal velocity (V2) and VTI ($VTI_{AO}$) in the same view. V1/V2 ratio was calculated in the pre-treatment period to determine AVS development. Aortic valve area (AVA) was obtained at each time point by the continuity equation: $AVA=CSA_{LVOT}\times(VTI_{LVOT}/TI_{AO})$. Aortic valve thickness in its middle portion was measured at end-diastole in a zoomed parasternal long-axis view at baseline, before randomized therapy, and at the final echocardiographic exam.

The average of three consecutive cardiac cycles was used for each measurement. Special care was taken to obtain similar imaging planes on serial examinations by reviewing previous recordings before follow-up study. All echocardiographic imaging and measurements were performed throughout the protocol by the same experienced investigator blinded to randomized treatment assignment.

Histomorphometry

The ascending aorta and aortic valve were opened longitudinally and the 3 valvular cusps were separated. Two cusps were immediately frozen in an embedding medium (OCT Tissue-Tek; Sakura, USA) and stored at −80° C. The third cusp was immersion-fixed in 10% buffered formalin at 4° C. for 24 hours and embedded in paraffin. Stained or immunohistochemically labeled tissue sections obtained from the central third of each cusp were analyzed with a computer-based digitizing image system (Image Pro Plus, version 5.1) using a light microscope (BX41, Olympus) connected to a digital video camera (Qcolor3, Olympus). The region of analysis (ROA) was composed of 1000 µm of the Valsalva sinus from the leaflet base and 500 µm of the leaflet from the leaflet base. Lesion area (LA) and leaflet lesion length (LLL) were measured.

Histochemistry

Hematoxylin-phloxin-safran, von Kossa and Sirius red (F3B, BDH, UK) stained sections were prepared for routine examination, tissue calcification and collagen studies respectively. Collagen fibers types I and III were quantified as previously described (13), on Sirius red picric acid stained sections under polarized light. For immunohistochemistry evaluation, all sections were preincubated with either mouse IgG2a monoclonal antibody against rabbit macrophage (RAM11, Dako, Canada) (1:100 dilution) or rabbit smooth muscle cell α-actin (Clone 1A4, Dako, Canada) (1:200 dilution). Species-appropriate biotinylated secondary antibodies were applied, followed by streptavidin horseradish peroxidase complex, visualized with azoethylcarbazol (AEC) and counterstained by Mayer's hematoxylin. Smooth muscle cells, macrophages and calcification areas were quantified in the ROA on digital images acquired at 40× magnification.

Images from each section were digitally captured with the same illumination settings, and automatic computer-based analysis was performed with the same color threshold for all specimens. Data were expressed as percent labelled area in ROA.

For assessment of tissue free cholesterol, 5 μm cryosections fixed in 4% paraformaldehyde in PBS (pH 7.4) were stained with filipin (13). Sections were incubated for 1 hour at room temperature in filipin complex (Sigma, Canada) dissolved in DMSO and diluted in PBS, mounted in Vectashield (Vector Laboratories, USA) and viewed by fluorescence microscopy using a Zeiss Axiovert 200M microscope with the DAPI filter set. Images were acquired with an AxioCam MRm digital camera mounted with a 0.63× C-mount adapter. Filipin data were expressed as arbitrary units of fluorescence intensity.

Statistical Analysis

Data are presented as mean±standard deviation. For the "pre-treatment" period, repeated measures analysis of variance (ANOVA) models were used to study the echocardiographic and serum measurements across time and between groups (treated vs. control groups). Models with time, group and group×time interaction as independent variables were used and comparisons between groups at a given time point were undertaken only in the presence of a significant group× time interaction. Otherwise, global conclusions were drawn based on the main group effects of the model. For the randomized treatment period, repeated measures analysis of covariance (ANCOVA) models were used to study the echocardiographic and serum measurements across time and between groups (treated vs. control groups), adjusted for the baseline value of the response variable. The group×time interaction was also included in the ANCOVA models and comparisons between groups at a given time point were undertaken only in the presence of a significant group×time interaction. Otherwise, global conclusions were drawn based on the main group effects of the model. Histological variables were compared between treated and control groups using Student t-test. Relationships between histomorphometry and echocardiographic variables were evaluated using Pearson correlation coefficient. All analyses were performed with SAS release 8.2 (SAS Institute Inc., Cary, N.C.) and conducted at the 0.05 significance level.

Results

Serum Lipids and Calcemia

There was no significant difference between groups during the pre-treatment period (the hypercholesterolemic diet period) for serum levels of total cholesterol (P=0.942), HDL-cholesterol (P=0.787), triglycerides (P=0.906), and calcemia (P=0.727). During the 2-week treatment period, total cholesterol levels were also statistically similar in both groups (P=0.470). Values were 20.46±3.52 mmol/L and 20.13±5.18 mmol/L at the time of randomization and 13.78±6.24 mmol/L and 17.57±10.32 mmol/L at end of treatment in the control and treated groups respectively. There was no statistically significant difference between groups for HDL-cholesterol levels during the treatment period (P=0.374). HDL-cholesterol was 0.500±0.20 mmol/L and 0.50±0.15 mmol/L at the time of randomization and 0.39±0.17 mmol/L and 0.45±0.17 mmol/L at end of treatment. During this period, triglyceride levels were also similar (P=0.544). There was no significant difference between groups for calcemia during the treatment period (P=0.832), with values of 3.31±0.29 mmol/L and 3.15±0.37 mmol/L before randomization and 3.22±0.11 mmol/L and 3.22±0.12 mmol/L at the end of treatment in both groups.

Development of AVS During the Period of Hypercholesterolemic Diet and Vitamin $D_2$ Supplementation AVS induction time by the cholesterol plus vitamin $D_2$ diet was similar for control and treated groups (12.8±2.2 vs. 13.0±2.9 weeks; P=0.852). There was a significant difference between AVA at baseline and at the end of the hypercholesterolemic diet period (P<0.0001). AVA decreased in both groups, and values were almost identical between control and treated rabbits (from 24.2±4.1 $mm^2$ at baseline to 19.0±2.7 $mm^2$ in controls and from 24.7±3.9 $mm^2$ to 19.1±2.6 $mm^2$ in the treated group). There were therefore no significant differences in AVA between groups during the period of AVS development (P=0.852). Thus, AVA decreased by 20.5±4.2% and 21.6±3.7% before randomized treatment in the control and treated groups.

The $V_1/V_2$ ratio was also significantly different between measurements at baseline and at the end of hypercholesterolemic diet (P<0.0001). $V_1/V_2$ ratios decreased between these time points with no significant differences among groups (P=0.914).

Evolution of AVS with Treatment—Echocardiography

As illustrated in FIG. 1, during the treatment period (from AVS detection to after 2 weeks of treatment), significant group×time interaction was observed for AVA (P=0.013). Using repeated measures ANCOVA models, echocardiographic measurements revealed significant increases of AVA in the treated group as compared to controls after 7 days (21.9±3.6 $mm^2$ vs. 19.6±1.8 $mm^2$, P=0.019) (relative increases of 14.2±3.5% vs. 3.9±3.4%), 10 days (23.0±4.1 $mm^2$ vs. 20.3±2.4 $mm^2$, P=0.006) (relative increases of 19.8±3.5% vs. 7.6±4.2%) and 14 days of treatment (23.8±3.1 $mm^2$ vs. 21.3±2.4 $mm^2$, P=0.012) (relative increases of 24.6±2.0% vs. 12.9±3.5%).

Figure 2:
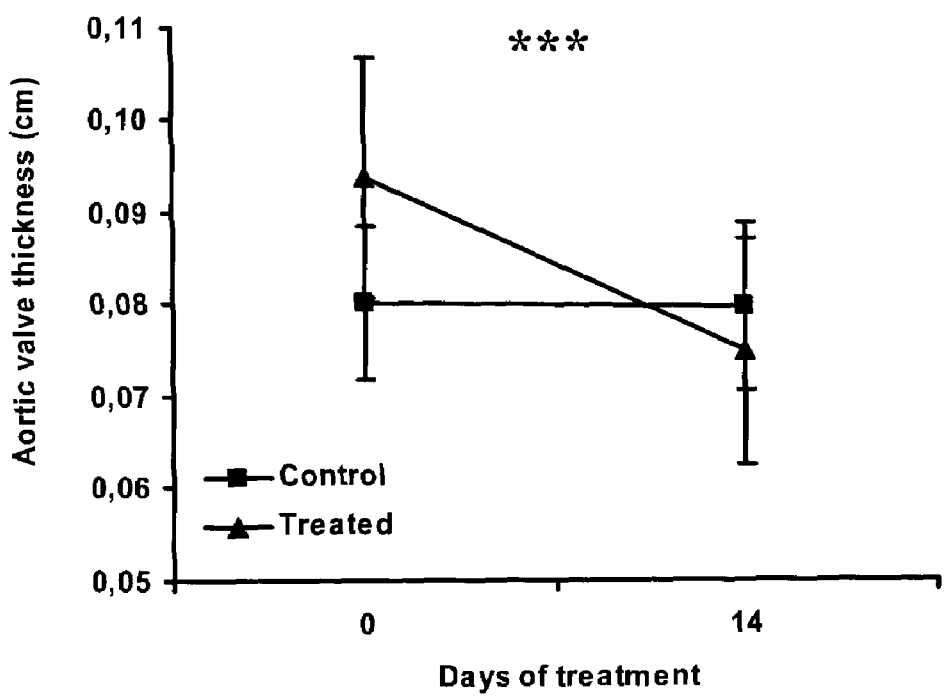
FIG. 2 illustrates aortic valve thickness values obtained through echocardiographic measurements during the ApoA-1 mimetic peptide treatment period. Day "0" corresponds to the end of cholesterol plus vitamin $D_2$ diet and the beginning of ApoA-1 mimetic peptide treatment period, ***P<0.001.

Aortic valve thickness was assessed by echocardiography and measured before randomized therapy and after 14 days of treatment (See FIG. 2). Significant group×time interaction was also observed for aortic valve thickness (P=0.005). No significant difference was found between groups at the randomization time point but a significant decrease of aortic valve thickness was observed in the treated group as compared to the control group after 14 days of treatment. Aortic valve thickness was 0.094±0.034 cm before randomization and 0.075±0.033 cm at end of treatment in treated rabbits whereas it was 0.080±0.024 cm and 0.080+0.026 cm at both time points in controls.

Histology

All the animals presented aortic valve lesions. Lesions consisted in a cap of neotissue composed of multiple layers of foam cells giving place gradually to fibrotic material sparse with foam cells from about half-way deep in the lesion. Lesions were generally progressing from the sinotubular area, covering the whole sinus of Valsalva and extending to the cusp base and up to one half to two thirds of the proximal leaflet arterialis. In contrast, lesions on the leaflet ventricularis were not common and were less severe.

Histomorphometry

Figure 3:
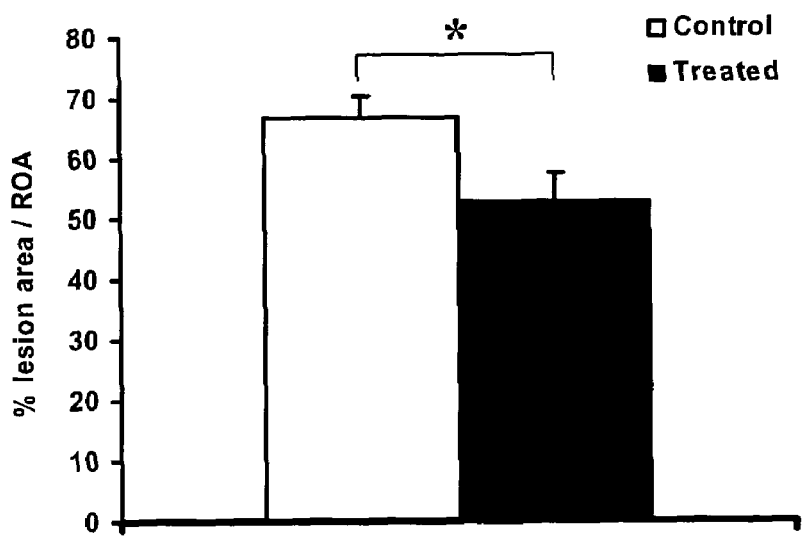
FIG. 3 illustrates a comparison of the percentage of lesion area (LA) over the region of analysis (ROA) in aortic valves from control and treated groups, *P=0.032.
Figure 4:
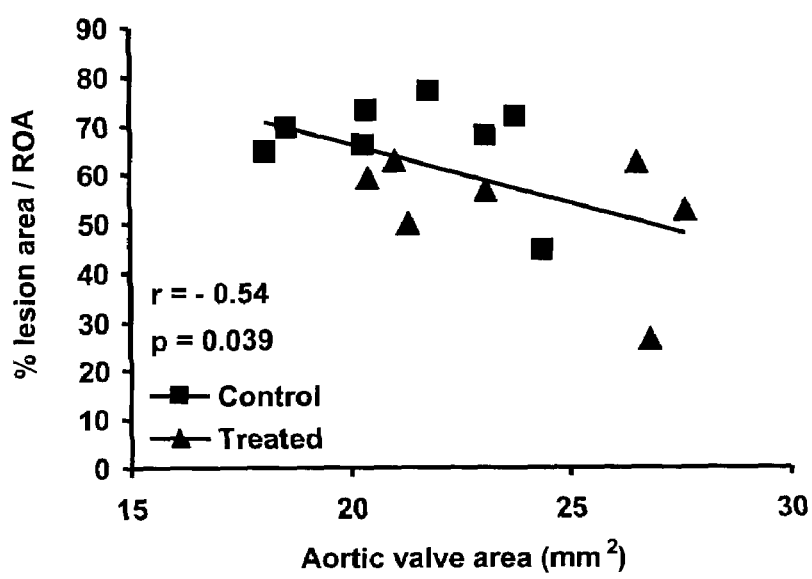
FIG. 4 illustrates a correlation between aortic valve area (AVA) and the percentage of lesion area (LA) over the region of analysis (ROA) in aortic valves from both groups.

As shown in FIG. 3 the percentage of LA per ROA decreased significantly in the ApoA-1 mimetic peptide treated group as compared to the control group (52.8±12.5%/ROA vs. 66.7±9.9%/ROA, P=0.032). Interestingly, when the percentage of LA/ROA on histomorphometry and echocardiography-determined AVA from both groups were pooled, a negative correlation was found between the percentage of LA/ROA and AVA (r=−0.54, P=0.039, FIG. 4). Similarly, analysis of pooled data from both groups revealed a negative correlation between AVA and % LLL (Ae. the percentage of total leaflet length occupied by lesion or LLL/total leaflet length×100) (r=−0.70, P=0.004). However, the difference between the treated and control groups for % LLL did not reach statistical significance (55.7±24.3% vs. 72.3±11.7%, P=0.109).

Histochemistry

Figure 5:
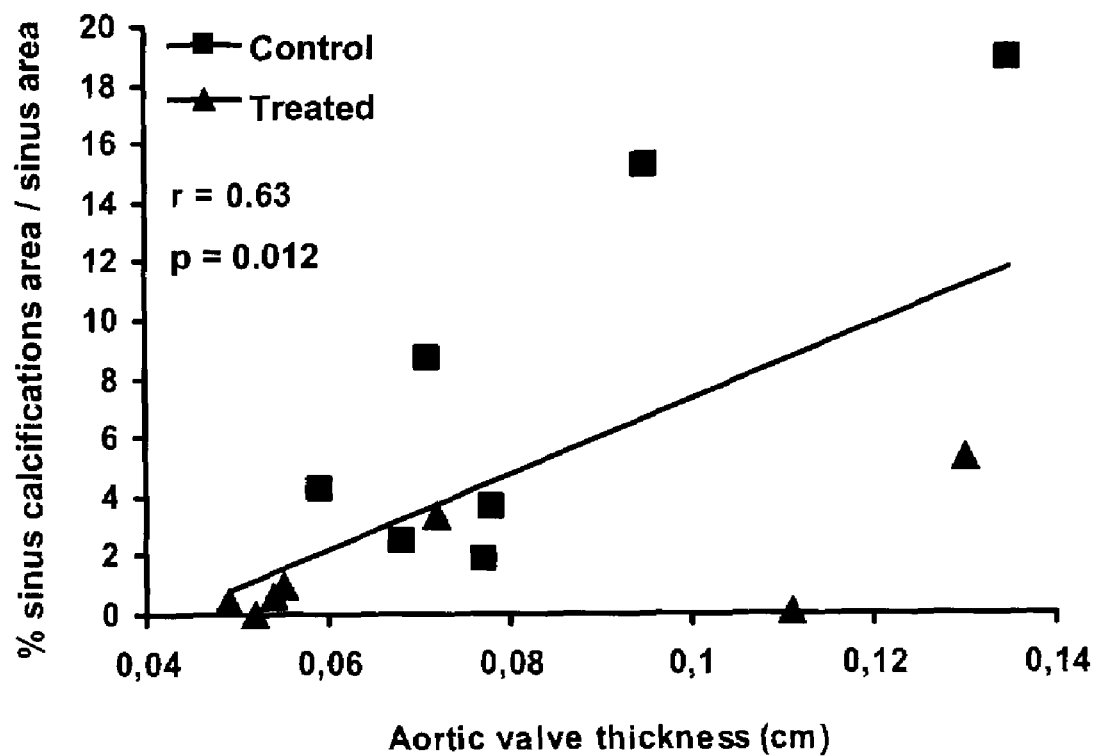
FIG. 5 illustrates the correlation between aortic valve thickness on echocardiography and the percentage of calcification area in the sinus of Valsalva area in animals from both groups. Note that a value (square) from one control animal is hidden behind two triangles at the bottom left of the figure.

Foci of calcifications were observed in the majority of animals The percentages of rabbits with calcium deposits in the lesion core in the sinuses of Valsalva were 57% (4/7) in the treated group and 88% (7/8) in controls. Quantification of the percentage of the sinus of Valsalva area occupied by calcifications on von Kossa staining revealed a strong trend towards a 77% decrease in the treated group compared to controls (1.6±2.0% vs. 6.9±6.7%; P=0.063). This percentage of calcification foci area within the sinus area was significantly correlated with echocardiography-determined aortic valve thickness (r=0.63, P=0.012) using pooled data from both study groups (FIG. 5).

Free cholesterol, as detected by filipin staining, was present throughout the whole aortic valve lesion areas in almost all control animals, whereas the fluorescent signal tended to be lower at the luminal edge of lesions in most animals treated with the ApoA-1 mimetic peptide. Assessment of the fluorescent signal within the first 10 μm at the luminal edge of lesions showed a 41% decrease in free cholesterol in treated animals compared to controls but this difference did not reach statistical significance (221±54 vs. 377±229 arbitrary units of fluorescence intensity, P=0.231). The macrophage areas (34.5%) were about twice as large as α-actin positive areas (17.1%), with no significant differences between groups. The percentage of collagen type III fibers (light green) was higher than collagen type I fibers (red-yellow) in the ROA (19.7±5.5%/ROA for type III vs. 6.6±4.1%/ROA for type I in controls, P=0.00009; 19.1±11.3%/ROA for type III vs. 5.5±5.6%/ROA for type I in treated rabbits, P=0.015,). Percentages of collagen fibers (types I and II) in the ROA were however similar between both groups (P=0.671 and P=0.883 respectively).

Discussion

These experiments demonstrate that infusions of an ApoA-1 mimetic peptide lead to significant regression of experimental AVS. Compared to the control group, ApoA-1 mimetic peptide infusions induced greater improvement of AVA and a significant reduction in aortic valve thickness. These favorable changes in AVS severity on echocardiography were accompanied on histological sections by a significant decrease in lesion extent in the leaflet base region and a strong trend towards decreased calcifications.

A rabbit model of AVS developed by Drolet et al. (12) in which aortic valve calcification occurs significantly and reproducibly was used, allowing to mimic the clinical condition. After a cholesterol-enriched diet and vitamin $D_2$ supplementation for approximately 13 weeks, echocardiographic measurements revealed a 21% decrease in AVA. Two-dimensional imaging showed increased valve thickness and echogenicity compatible with leaflet sclerosis and areas of calcification. Histological examination confirmed leaflet thickening and calcium deposition both in the sinuses of Valsalva and at the leaflet base. This study provides echocardiographic and histological evidence of the beneficial effects of an ApoA-1 mimetic peptide on experimental calcific AVS. The increase in AVA was observed as early as 7 days after the initiation of active treatment, to reach an improvement of 24% at 14 days. AVA indeed almost returned, with the ApoA-1 mimetic peptide infusions, to the normal value present prior to starting the hypercholesterolemic diet. In contrast, discontinuation of the cholesterol-enriched diet with vitamin $D_2$ supplementation in the control group (to mimic lipid-lowering) only led to a mild increase in AVA, which confirms the beneficial effects of the peptide. Aortic valve thickness was also significantly reduced after only 14 days of treatment with the peptide, as shown by echocardiography. Interestingly, AVA determined by echocardiography correlated inversely with indices of lesion extent on histology. ApoA-1 mimetic peptide infusions also led to a significant reduction in the percentage of lesion area in the region of histological analysis around the valvular leaflet base. Furthermore, the large reduction in the extent of valvular calcifications that almost reached statistical significance at the arbitrarily chosen 0.05 level is likely to be of clinical importance, given that calcific AVS of the elderly is the most frequent form of stenosis encountered in developed countries. This suggests that the presence of aortic valve calcifications not only does not preclude obtaining favorable results with the peptide but that this approach may even regress the valvular calcifications themselves. This finding may also be applicable to mitral valve and/or annular calcifications.

An ApoA-1 mimetic peptide complexed with phospholipids stimulates reverse cholesterol transport in a manner similar to native ApoA-1 (14). The higher circulating levels of total cholesterol in rabbits treated with the peptide compared to controls (observed after 2 weeks of treatment) may indicate enhanced mobilization of tissue cholesterol.

This example suggests that similar results are obtainable in humans using any suitable HDL-based therapy, such as for example one or more infusion(s) or bolus(es) of HDL or peptide (with or without lipids) with HDL-like effects, orally administered HDL-mimetic agents, and/or the administration of cholesteryl ester transfer protein (CETP) modulators, or scavenger receptor class B, member 1 (SRB1) modulators or liver X receptor (LXR)/retinoid X receptor (RXR) agonists, or ATP-binding cassette transporter-1 (ABCA1) agonists, or peroxisome proliferator-activated receptor (PPAR) agonists, among others.

While the experiments described herein concerned the regulation aortic valve stenosis, one of ordinary skilled in the art will readily appreciate that these experiments may be predictive of biological effects in humans or other mammals and/or may serve as models for use of the present invention in humans or other mammals for any other similar valve diseases.

Although the present invention has been described hereinabove by way of preferred embodiments thereof, it can be modified, without departing from the spirit and nature of the subject invention as defined in the appended claim.

REFERENCES

1. Freeman R V, Otto C M. Spectrum of calcific aortic valve disease: pathogenesis, disease progression, and treatment strategies. Circulation 2005; 111:3316-26.
2. Carabello B A. Aortic stenosis. N Engl J Med 2002; 346: 677-82.
3. Nissen S E, Nicholls S J, Sipahi I. Effect of very high intensity statin therapy on regression of coronary atherosclerosis. The ASTEROID trial. JAMA. 2006; 295: 1556-65.
4. Cowell S J, Newby D E, Prescott R J, et al. Scottish Aortic Stenosis and Lipid Lowering Trial, Impact on Regression (SALTIRE) Investigators. A randomized trial of intensive lipid-lowering therapy in calcific aortic stenosis. N Engl J Med 2005; 352:2389-97.

5. Ameli S, Hultgardh-Nilsson A, Cercek B, et al. Recombinant apolipoprotein A-I Milano reduces intimal thickening after balloon injury in hypercholesterolemic rabbits. Circulation 1994; 90:1935-41.
6. Shah P K, Yano J, Reyes O, et al. High-dose recombinant apolipoprotein A-I(milano) mobilizes tissue cholesterol and rapidly reduces plaque lipid and macrophage content in apolipoprotein e-deficient mice. Potential implications for acute plaque stabilization. Circulation 2001; 103:3047-50.
7. Nissen S E, Tsunoda T, Tuzcu E M, et al. Effect of recombinant ApoA-1 Milano on coronary atherosclerosis in patients with acute coronary syndromes: a randomized controlled trial. JAMA 2003; 290:2292-300.
8. Tardif J C, Grégoire J, L'Allier P L, et al. Effects of reconstituted high-density lipoprotein infusions on coronary atherosclerosis: a randomized controlled trial. JAMA 2007; 297:1675-82.
9. Meyers C D, Kashyap M L. Pharmacologic augmentation of high-density lipoproteins: mechanisms of currently available and emerging therapies. Curr Opin Cardiol 2005; 20:307-12.
10. Khan M, Lalwani N D, Drake S L, Crockatt J G, Dasseux J L H. Single-dose intravenous infusion of ETC-642, a 22-Mer ApoA-1 analogue and phospholipids complex, elevates HDL-C in atherosclerosis patients. Circulation 2003; 108(Suppl):IV-563-4.
11. Bodary P F, Shen Y, Westrick R J, et al. Gene transfer of an APO-A-I mimetic peptide reduces atherosclerosis in mice. J Am Coll Cardiol. 2004; 43(Suppl A):465A-6.
12. Drolet M C, Arsenault M, Couet J. Experimental aortic valve stenosis in rabbits. J Am Coll Cardiol 2003; 41:1211-7.
13. Busseuil D, Zeller M, Cottin Y, et al. Late neointimal tissue growth behind the stent after intravascular gamma-radiation. Int J Radiat Oncol Biol Phys 2004; 58:259-66.
14. Navab M, Anantharamaiah G M, Reddy S T, et al. Apolipoprotein A-I mimetic peptides. Arterioscler Thromb Vasc Biol 2005; 25:1325-31.
15. Navab M, Anantharamaiah G M, Reddy S T, et al. Human apolipoprotein A-I and A-I mimetic peptides: potential for atherosclerosis reversal. Curr Opin Lipidol 2004; 15:645-9.

What is claimed is:

1. A method for treating an aortic valve stenosis in a subject, said method comprising administering to a subject in need of treatment for an aortic valve stenosis a therapeutically effective amount of a peptide/phospholipid complex, wherein the peptide is of the following Formula (I):

$$X_1-X_2-X_3-X_4-X_5-X_6-X_7-X_8-X_9-X_{10}-X_{11}-X_{12}-X_{13}-X_{14}-X_{15}-X_{16}-X_{17}-X_{18}-X_{19}-X_{20}-X_{21}-X_{22}$$ Formula (I)

or a pharmaceutically acceptable salt thereof, wherein:

$X_1$ is Pro (P), Ala (A), Gly (G), Gln (Q), Asn (N), Asp (D) or D-Pro (p);
$X_2$ is an aliphatic amino acid;
$X_3$ is Leu (L) or Phe (F);
$X_4$ is an acidic amino acid;
$X_5$ is Leu (L) or Phe (F);
$X_6$ is Leu (L) or Phe (F);
$X_7$ is a hydrophilic amino acid;
$X_8$ is an acidic or a basic amino acid;
$X_9$ is Leu (L) or Gly (G);
$X_{10}$ is Leu (L), Trp (W) or Gly (G);
$X_{11}$ is a hydrophilic amino acid;
$X_{12}$ is a hydrophilic amino acid;
$X_{13}$ is Gly (G) or an aliphatic amino acid;
$X_{14}$ is Leu (L), Trp (W), Gly (G) or Nal;
$X_{15}$ is a hydrophilic amino acid;
$X_{16}$ is a hydrophobic amino acid;
$X_{17}$ is a hydrophobic amino acid;
$X_{18}$ is Gln (Q), Asn (N) or a basic amino acid;
$X_{19}$ is Gln (Q), Asn (N) or a basic amino acid;
$X_{20}$ is a basic amino acid;
$X_{21}$ is an aliphatic amino acid; and
$X_{22}$ is a basic amino acid.

2. The method of claim 1, wherein administering said complex includes injecting said complex in said subject.

3. The method of claim 2, wherein said complex is injected at a dosage of peptide of from about 1 µg to about 10 g per kg body weight of said subject.

4. The method of claim 3, wherein said complex is injected at a dosage of peptide of from about 1 mg to about 0.5 g per kg body weight of said subject.

5. The method of claim 4, wherein said complex is injected a dosage of peptide of about 25 mg per kg body weight of said subject.

6. The method of claim 1, wherein the peptide has the sequence set forth in SEQ ID NO: 1 or a pharmaceutically acceptable salt thereof.

7. The method of claim 1, wherein said subject is a mammal.

8. The method of claim 7, wherein said subject is a human.

9. The method of claim 1, wherein:

$X_1$ is Pro (P), Gly (G), Ala (A), Gln (Q), Asn (N), Asp (D) or D-Pro (p);
$X_2$ is Ala (A), Val (V) or Leu (L);
$X_4$ is Asp (D) or Glu (E);
$X_7$ is Lys (K), Arg (R), Orn, Asn (N) or Glu (E);
$X_8$ is Asp (D), Arg (R) or Glu (E);

$X_{11}$ is Asn (N), Gln (Q), Glu (E) or Arg (R);
$X_{12}$ is Asp (D), Glu (E) or Asn (N);
$X_{13}$ is Leu (L), Gly (G) or Aib;
$X_{15}$ is Asp (D), Glu (E), Gln (Q) or Lys (K);
$X_{16}$ is Ala (A), Trp (W), Gly (G), Leu (L), Phe (F) or NaI;
$X_{17}$ is Leu (L), Gly (G) or NaI;
$X_{18}$ is Lys (K), Orn, Gln (Q) or Asn (N);
$X_{19}$ is Lys (K), Orn, Gln (Q) or Asn (N);
$X_{20}$ is Lys (K) or Orn;
$X_{21}$ is Leu (L); or
$X_{22}$ is Lys (K) or Orn.

10. The method of claim 1, wherein:
$X_2$ is Val (V);
$X_3$ is Leu (L);
$X_5$ is Leu (L);
$X_6$ is Phe (F);
$X_7$ is Arg (R) or Lys (K);
$X_8$ is Gln (E);
$X_9$ is Leu (L);
$X_{10}$ is Len (L);
$X_{11}$ is Asn (N) or Glu (Q);
$X_{12}$ is Glu (E); or
$X_{15}$ is Glu (E).

11. The method of claim 1, wherein:
$X_1$ is Pro (P), Gly (G), Ala (A), Gln (Q), Asn (N), Asp (D) or D-Pro (p);
$X_2$ is Ala (A), Val (V) or Leu (L);
$X_4$ is Asp (D) or Glu (E);
$X_7$ is Lys (K), Arg (R), Orn, Asn (N) or Glu (E);
$X_8$ is Asp (D), Arg (R) or Glu (E);
$X_{11}$ is Asn (N), Gln (Q), Glu (E) or Arg (R);
$X_{12}$ is Asp (D), Glu (E) or Asn (N);
$X_{13}$ is Leu (L), Gly (G) or Aib;
$X_{15}$ is Asp (D), Glu (E), Gln (Q) or Lys (K);
$X_{16}$ is Ala (A), Trp (W), Gly (G), Leu (L), Phe (F) or NaI;
$X_{17}$ is Leu (L), Gly (G) or NaI;
$X_{18}$ is Lys (K), Orn, Gln (Q) or Asn (N);
$X_{19}$ is Lys (K), Orn, Gln (Q) or Asn (N);
$X_{20}$ is Lys (K) or Orn;
$X_{21}$ is Leu (L); and
$X_{22}$ is Lys (K) or Orn.

12. The method of claim 1, wherein:
$X_2$ is Val (V);
$X_3$ is Leu (L);
$X_5$ is Leu (L);
$X_6$ is Phe (F);
$X_7$ is Arg (R) or Lys (K);
$X_8$ is Glu (E);
$X_9$ is Leu (L);
$X_{10}$ is Leu (L);
$X_{11}$ is Asn (N) or Glu (Q);
$X_{12}$ is Glu (E); and
$X_{15}$ is Glu (E).

13. The method of claim 1, wherein the phospholipid comprises egg sphingomyelin.

14. The method of claim 1, wherein the phospholipid comprises 1,2-dipalmitoyl-sn-glycero-3-phosphocholine.

15. The method of claim 1, wherein the phospholipid comprises egg sphingomyelin and 1,2-dipalmitoyl-sn-glycero-3-phosphocholine.

16. The method of claim 15, wherein the weight ratio of peptide:egg sphingomyelin: 1,2-dipalmitoyl-sn-glycero-3-phosphocholine is 1:1:1.

* * * * *

UNITED STATES PATENT AND TRADEMARK OFFICE
CERTIFICATE OF CORRECTION

PATENT NO. : 8,163,699 B2
APPLICATION NO. : 12/227872
DATED : April 24, 2012
INVENTOR(S) : Jean-Claude Tardif Page 1 of 1

It is certified that error appears in the above-identified patent and that said Letters Patent is hereby corrected as shown below:

Column 41
Line 49, "Gln (0)" should read as --Gln (Q)--
Line 63, "NaI" should read as --Nal--

Column 42
Line 53, "a dosage" should read as --at a dosage--
Line 62, "Gin" should read as --Gln--

Column 43
Line 4, "Gin" should read as --Gln--
Line 5, "NaI" should read as --Nal--
Line 6, "NaI" should read as --Nal--
Line 18, "Gin" should read as --Glu--
Line 20, "Len" should read as --Leu--
Line 21, "Glu (Q)" should read as --Gln (Q)--
Line 31, "Gin" should read as --Gln--

Column 44
Line 2, "Gin" should read as --Gln--
Line 3, "NaI" should read as --Nal--
Line 4, "NaI" should read as --Nal--
Line 5, "Gin" should read as --Gln--
Line 6, "Gin" should read as --Gln--
Line 19, "Glu (Q)" should read as --Gln (Q)--

Signed and Sealed this
Tenth Day of July, 2012

David J. Kappos
*Director of the United States Patent and Trademark Office*

SEQUENCE LISTING

```
<160> NUMBER OF SEQ ID NOS: 51

<210> SEQ ID NO 1
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 1

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 2
<211> LENGTH: 22
<212> TYPE: PRT
<213> ORGANISM: Artificial Sequence
<220> FEATURE:
<223> OTHER INFORMATION: Segrest consensus sequence

<400> SEQUENCE: 2

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 3
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (16)..(16)
<223> OTHER INFORMATION: Xaa=Nal

<400> SEQUENCE: 3

Pro Val Leu Asp Leu Phe Arg Glu Leu Leu Asn Glu Leu Leu Glu Xaa
1               5                   10                  15
```

Leu Lys Gln Lys Leu Lys
            20

<210> SEQ ID NO 4
<211> LENGTH: 23
<212> TYPE: PRT
<213> ORGANISM: Artificial Sequence
<220> FEATURE:
<223> OTHER INFORMATION: ApoA-I mimic

<400> SEQUENCE: 4

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 5
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 5

Pro Val Leu Asp Leu Phe Arg Glu Leu Leu Asn Glu Leu Leu Glu Trp
1               5                   10                  15

Leu Lys Gln Lys Leu Lys
            20

<210> SEQ ID NO 6
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 6

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 7
<211> LENGTH: 23
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (1)..(1)
<223> OTHER INFORMATION: Xaa=D-Pro

<400> SEQUENCE: 7

Xaa Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 8
<211> LENGTH: 22
<212> TYPE: PRT
<213> ORGANISM: Artificial Sequence
<220> FEATURE:
<223> OTHER INFORMATION: ApoA-I mimic
<220> FEATURE:

```
<221> NAME/KEY: MOD_RES
<222> LOCATION: (13)..(13)
<223> OTHER INFORMATION: Xaa=Aib

<400> SEQUENCE: 8

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 9
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 9

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 10
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 10

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 11
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 11

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 12
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (17)..(17)
<223> OTHER INFORMATION: Xaa=Nal

<400> SEQUENCE: 12

Pro Val Leu Asp Leu Phe Arg Glu Leu Leu Asn Glu Leu Leu Glu Ala
1               5                   10                  15

Xaa Lys Gln Lys Leu Lys
            20
```

```
<210> SEQ ID NO 13
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 13

Pro Val Leu Asp Leu Phe Lys Glu Leu Leu Gln Glu Leu Leu Glu Ala
1               5                   10                  15
Leu Lys Gln Lys Leu Lys
            20

<210> SEQ ID NO 14
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 14

Pro Val Leu Asp Leu Phe Arg Glu Leu Leu Asn Glu Leu Leu Glu Ala
1               5                   10                  15
Gly Lys Gln Lys Leu Lys
            20

<210> SEQ ID NO 15
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 15

Gly Val Leu Asp Leu Phe Arg Glu Leu Leu Asn Glu Gly Leu Glu Ala
1               5                   10                  15
Leu Lys Gln Lys Leu Lys
            20

<210> SEQ ID NO 16
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (18)..(18)
<223> OTHER INFORMATION: Xaa=Orn
<220> FEATURE:
<221> NAME/KEY: MOD_RES
<222> LOCATION: (20)..(20)
<223> OTHER INFORMATION: Xaa=Orn
<220> FEATURE:
<221> NAME/KEY: MOD_RES
<222> LOCATION: (22)..(22)
<223> OTHER INFORMATION: Xaa=Orn

<400> SEQUENCE: 16

Pro Val Leu Asp Leu Phe Arg Glu Leu Leu Asn Glu Leu Leu Glu Ala
1               5                   10                  15
Leu Xaa Gln Xaa Leu Xaa
            20

<210> SEQ ID NO 17
<211> LENGTH: 22
<212> TYPE: PRT
```

```
<213> ORGANISM: Artificial Sequence
<220> FEATURE:
<223> OTHER INFORMATION: ApoA-I mimic

<400> SEQUENCE: 17

Pro Val Leu Asp Leu Phe Arg Glu Leu Trp Asn Glu Leu Leu Glu Ala
1               5                   10                  15

Leu Lys Gln Lys Leu Lys
            20

<210> SEQ ID NO 18
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 18

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 19
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 19

Pro Val Leu Glu Leu Phe Lys Glu Leu Leu Gln Glu Leu Leu Glu Ala
1               5                   10                  15

Leu Lys Gln Lys Leu Lys
            20

<210> SEQ ID NO 20
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 20

Gly Val Leu Asp Leu Phe Arg Glu Leu Leu Asn Glu Leu Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (1)..(1)
<223> OTHER INFORMATION: Xaa=D-Pro

<400> SEQUENCE: 21

Xaa Val Leu Asp Leu Phe Arg Glu Leu Leu Asn Glu Gly Leu Glu Ala
1               5                   10                  15

Leu Lys Gln Lys Leu Lys
            20
```

```
<210> SEQ ID NO 22
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 22

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 23
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (1)..(1)
<223> OTHER INFORMATION: Xaa=D-Pro

<400> SEQUENCE: 23

Xaa Val Leu Asp Leu Phe Arg Glu Leu Leu Asn Glu Leu Leu Glu Ala
1               5                   10                  15

Leu Lys Gln Lys Leu Lys
            20

<210> SEQ ID NO 24
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 24

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 25
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 25

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 26
<211> LENGTH: 22
<212> TYPE: PRT
<213> ORGANISM: Artificial sequence
<220> FEATURE:
<223> OTHER INFORMATION: ApoA-I mimic

<400> SEQUENCE: 26

Pro Leu Leu Glu Leu Phe Lys Glu Leu Leu Gln Glu Leu Leu Glu Ala
1               5                   10                  15
```

Leu Lys Gln Lys Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (13)..(13)
<223> OTHER INFORMATION: Xaa=Aib

<400> SEQUENCE: 27

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 28
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 28

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 29
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (14)..(14)
<223> OTHER INFORMATION: Xaa=Nal

<400> SEQUENCE: 29

Pro Val Leu Asp Leu Phe Arg Glu Leu Leu Asn Glu Leu Xaa Glu Ala
1               5                   10                  15

Leu Lys Gln Lys Leu Lys
            20

<210> SEQ ID NO 30
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 30

Pro Val Leu Asp Leu Phe Arg Glu Leu Leu Asn Glu Leu Trp Glu Ala
1               5                   10                  15

Leu Lys Gln Lys Leu Lys
            20

<210> SEQ ID NO 31
<211> LENGTH: 22
<212> TYPE: PRT

```
<213> ORGANISM: Artificial Sequence
<220> FEATURE:
<223> OTHER INFORMATION: ApoA-I mimic

<400> SEQUENCE: 31

Ala Val Leu Asp Leu Phe Arg Glu Leu Leu Asn Glu Leu Leu Glu Ala
1               5                   10                  15
Leu Lys Gln Lys Leu Lys
            20

<210> SEQ ID NO 32
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 32

Gln Val Leu Asp Leu Phe Arg Glu Leu Leu Asn Glu Leu Leu Glu Ala
1               5                   10                  15
Leu Lys Gln Lys Leu Lys
            20

<210> SEQ ID NO 33
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (7)..(7)
<223> OTHER INFORMATION: Xaa=Orn
<220> FEATURE:
<221> NAME/KEY: MOD_RES
<222> LOCATION: (18)..(18)
<223> OTHER INFORMATION: Xaa=Orn
<220> FEATURE:
<221> NAME/KEY: MOD_RES
<222> LOCATION: (20)..(20)
<223> OTHER INFORMATION: Xaa=Orn
<220> FEATURE:
<221> NAME/KEY: MOD_RES
<222> LOCATION: (22)..(22)
<223> OTHER INFORMATION: Xaa=Orn

<400> SEQUENCE: 33

Pro Val Leu Asp Leu Phe Xaa Glu Leu Leu Asn Glu Leu Leu Glu Ala
1               5                   10                  15
Leu Xaa Gln Xaa Leu Xaa
            20

<210> SEQ ID NO 34
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 34

Asn Val Leu Asp Leu Phe Arg Glu Leu Leu Asn Glu Leu Leu Glu Ala
1               5                   10                  15
Leu Lys Gln Lys Leu Lys
            20

<210> SEQ ID NO 35
<211> LENGTH: 22
<212> TYPE: PRT
```

-continued

<213> ORGANISM: Artificial Sequence
<220> FEATURE:
<223> OTHER INFORMATION: ApoA-I mimic

<400> SEQUENCE: 35

Pro Val Leu Asp Leu Phe Arg Glu Leu Leu Asn Glu Leu Gly Glu Ala
1               5                   10                  15

Leu Lys Gln Lys Leu Lys
            20

<210> SEQ ID NO 36
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 36

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 37
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 37

Pro Val Leu Asp Leu Phe Arg Glu Leu Leu Asn Glu Leu Leu Glu Phe
1               5                   10                  15

Leu Lys Gln Lys Leu Lys
            20

<210> SEQ ID NO 38
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 38

Pro Val Leu Glu Leu Phe Asn Asp Leu Leu Arg Glu Leu Leu Glu Ala
1               5                   10                  15

Leu Gln Lys Lys Leu Lys
            20

<210> SEQ ID NO 39
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 39

Pro Val Leu Glu Leu Phe Asn Asp Leu Leu Arg Glu Leu Leu Glu Ala
1               5                   10                  15

Leu Lys Gln Lys Leu Lys
            20

<210> SEQ ID NO 40
<211> LENGTH: 22
<212> TYPE: PRT

<213> ORGANISM: Artificial Sequence
<220> FEATURE:
<223> OTHER INFORMATION: ApoA-I mimic

<400> SEQUENCE: 40

Pro Val Leu Glu Leu Phe Lys Glu Leu Leu Asn Glu Leu Leu Asp Ala
1               5                   10                  15

Leu Arg Gln Lys Leu Lys
            20

<210> SEQ ID NO 41
<211> LENGTH: 22
<212> TYPE: PRT
<213> ORGANISM: Artificial sequence
<220> FEATURE:
<223> OTHER INFORMATION: ApoA-I mimic

<400> SEQUENCE: 41

Pro Val Leu Asp Leu Phe Arg Glu Leu Leu Glu Asn Leu Leu Glu Ala
1               5                   10                  15

Leu Gln Lys Lys Leu Lys
            20

<210> SEQ ID NO 42
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 42

Pro Val Leu Glu Leu Phe Glu Arg Leu Leu Glu Asp Leu Leu Gln Ala
1               5                   10                  15

Leu Asn Lys Lys Leu Lys
            20

<210> SEQ ID NO 43
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 43

Pro Val Leu Glu Leu Phe Glu Arg Leu Leu Glu Asp Leu Leu Lys Ala
1               5                   10                  15

Leu Asn Gln Lys Leu Lys
            20

<210> SEQ ID NO 44
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 44

Asp Val Leu Asp Leu Phe Arg Glu Leu Leu Asn Glu Leu Leu Glu Ala
1               5                   10                  15

Leu Lys Gln Lys Leu Lys
            20

<210> SEQ ID NO 45
<211> LENGTH: 22
<212> TYPE: PRT

<213> ORGANISM: Artificial Sequence
<220> FEATURE:
<223> OTHER INFORMATION: ApoA-I mimic

<400> SEQUENCE: 45

Pro Ala Leu Glu Leu Phe Lys Asp Leu Leu Gln Glu Leu Leu Glu Ala
1               5                   10                  15

Leu Lys Gln Lys Leu Lys
            20

<210> SEQ ID NO 46
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (17)..(17)
<223> OTHER INFORMATION: Xaa=Nal

<400> SEQUENCE: 46

Pro Val Leu Asp Leu Phe Arg Glu Leu Leu Asn Glu Gly Leu Glu Ala
1               5                   10                  15

Xaa Lys Gln Lys Leu Lys
            20

<210> SEQ ID NO 47
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 47

Pro Val Leu Asp Leu Phe Arg Glu Leu Leu Asn Glu Gly Leu Glu Trp
1               5                   10                  15

Leu Lys Gln Lys Leu Lys
            20

<210> SEQ ID NO 48
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 48

Pro Val Leu Asp Leu Phe Arg Glu Leu Trp Asn Glu Gly Leu Glu Ala
1               5                   10                  15

Leu Lys Gln Lys Leu Lys
            20

<210> SEQ ID NO 49
<211> LENGTH: 22
<212> TYPE: PRT
<213> ORGANISM: Artificial Sequence
<220> FEATURE:
<223> OTHER INFORMATION: ApoA-I mimic
<220> FEATURE:
<221> NAME/KEY: MOD_RES
<222> LOCATION: (18)..(18)
<223> OTHER INFORMATION: Xaa=Orn
<220> FEATURE:
<221> NAME/KEY: MOD_RES
<222> LOCATION: (20)..(20)
<223> OTHER INFORMATION: Xaa=Orn
<220> FEATURE:

```
<221> NAME/KEY: MOD_RES
<222> LOCATION: (22)..(22)
<223> OTHER INFORMATION: Xaa=Orn

<400> SEQUENCE: 49

Pro Val Leu Asp Leu Phe Arg Glu Leu Leu Asn Glu Gly Leu Glu Ala
1               5                   10                  15

Leu Xaa Gln Xaa Leu Xaa
            20

<210> SEQ ID NO 50
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 50

Pro Val Leu Asp Leu Phe Arg Glu Leu Leu Asn Glu Gly Leu Glu Ala
1               5                   10                  15

Leu Gln Lys Lys Leu Lys
            20

<210> SEQ ID NO 51
<211> LENGTH: 22
<212> TYPE: PRT
<213> ORGANISM: Artificial Sequence
<220> FEATURE:
<223> OTHER INFORMATION: ApoA-I mimic

<400> SEQUENCE: 51

Pro Val Leu Glu Leu Phe Arg Glu Leu Leu Asn Glu Gly Leu Glu Ala
1               5                   10                  15

Leu Lys Gln Lys Leu Lys
            20
```